US006566513B1

(12) United States Patent
Guertler et al.

(10) Patent No.: US 6,566,513 B1
(45) Date of Patent: May 20, 2003

(54) **LENTIVIRUS FROM THE GROUP OF IMMUNODEFICIENCY VIRUSES OF DRILL MONKEYS (*MANDRILLUS LEUCOPHAEUS*) AND THEIR USE**

(75) Inventors: Lutz Gerhard Guertler, Greifswald (DE); Hans Peter Hauser, Marburg (DE); Yvette Beatrice Dongmo Deloko, Munich (DE); Leopold Zekeng, Cameroon (OA); Lazare Kaptue, Cameroon (OA)

(73) Assignee: Dade Behring Marburg GmbH (DE)

( * ) Notice: Subject to any disclaimer, the term of this patent is extended or adjusted under 35 U.S.C. 154(b) by 0 days.

(21) Appl. No.: 09/625,972

(22) Filed: Jul. 26, 2000

(30) Foreign Application Priority Data

Aug. 3, 1999 (DE) .......................................... 199 36 003

(51) Int. Cl.$^7$ ............................................... C07H 21/04
(52) U.S. Cl. ............................... 536/23.72; 435/235.1; 530/324; 530/826
(58) Field of Search ........................ 435/5, 235.1, 239; 530/350, 826, 324; 536/23.72

(56) References Cited

PUBLICATIONS

Chen et al., "Genetic Characterization of New West African Simian Immunodeficiency Virus SIVsm: Geographic Clustering Household–Derived SIV Strains with Human Immunodeficiency Virus Type 2 Subtypes and Genetically Diverse Viruses from a Single Feral Sooty Mangabey Troop," Journal of Virology, Jun. 1996, pp. 3617–3627, vol. 70, No. 6, American Society for Microbiology.

Clewley et al., "A Novel Simian Immunodeficiency Virus (SIVdrl) pol Sequence from the Drill Monkey, *Mandrillus leucophaeus*," Journal of Virology, Dec. 1998, pp. 10305–10309, vol. 72, No. 12, American Society for Microbiology.

Franchini et al., "Tenth Anniversary Perspectives on AIDS: Phylogenesis and Genetic Complexity of the Nonhuman Primate Retroviridae," AIDS Research and Human Retroviruses, 1994, pp. 1047–1060, vol. 10, No. 9, Mary Ann Liebert, Inc., Publishers.

Gao et al., "Letters to Nature: Human Infection by genetically diverse SIVsm–related HIV–2 in West Africa," Nature, Aug. 6, 1992, pp. 495–499, vol. 358.

Georges–Courbot, "Natural Infection of a Household Pet Red–Capped Mangabey (Cercocebus torquatus torquatus) with a New Simian Immunodeficiency Virus," Journal of Virology, Jan. 1998, pp. 600–608, vol. 72, No. 1, American Society for Microbiology.

Guertler et al., "Quantitative detection of viral RNA of HIV–1 subtypes by a PCR and a branched DNA technique," 12th World AIDS Conference, Extended version of the abstracts, 1. Basic Science, 1998, pp. 121–124, Monduzzi Editore, S.p.A., Bologna, Italy.

Hayami et al., "Survey of Simian Immunodeficiency Virus Among Nonhuman Primate Populations," Current Topics in Microbiology and Immunology, 1994, pp. 1–20, vol. 188, Springer–Verlag Berlin, Heidelberg, Germany.

Hirsch et al., "Characterization of a Novel Simian Immunodeficiency Virus (SIV) from L'Hoest Monkeys (Cercopithecus l'hoesti): Implications for the Origins of SIVmnd and Other Primate Lentiviruses," Journal of Virology, Feb. 1999, pp. 1036–1045, vol. 73, No. 2, American Society for Microbiology.

Khabbaz et al., "Brief Report: Infection of a Laboratory Worker with Simian Immunodeficiency Virus," The New England Journal of Medicine, Jan. 20, 1994, pp. 172–177, vol. 330, No. 3.

Korber et al. (ed.), Human Retroviruses and AIDS 1997: A Compilation and Analysis of Nucleic Acid and Amino Acid Sequences, title page, Theoretical Biology and Biophysics, Los Alamos National Laboratory, Los Alamos, New Mexico.

Kubo et al., "Abrogation of In Vitro Suppression of Human Immunodeficiency Virtus Type 1 (HIV–1) Replication Mediated by CD8+ T Lymphocytes of Asymptomatic HIV–1 Carriers by Staphylococcal Enterotoxin B and Phorbol Esters through Induction of Tumor Necrosis Factor Alpha," Journal of Virology, Oct. 1997, pp. 7560–7566, vol. 71, No. 10, American Society in Microbiology.

Saiki et al., "Reports: Primer–Directed Enzymatic Amplification of DNA with a Thermostable DNA Polymerase," Science, Jan. 29, 1988, pp. 487–491, vol. 239/.

Simon et al., "Correspondence: Sensitivity of screening kits for anti–HIV–1 subtype O antibodies," AIDS 1994, pp. 1628–1629, vol. 8, No. 11.

Tamalet et al., "Comparison of viral burden and phenotype of HIV–1 isolates from lymph nodes and blood," AIDS 1994, pp. 1083–1088, vol. 8, No. 8.

Thompson et al., "Clustal W: improving the sensitivity of progressive multiple sequence alignment through sequence weighting, position–specific gap penalties and weight matrix choice," Nucleic Acids Research, 1994, pp. 4673–4680, vol. 22, No. 22, Oxford University Press.

Tsujimoto et al., "Letters to Nature: Sequence of a novel simian immunodeficiency virus from a wild–caught African Mandrill," Nature, Oct. 12, 1989, pp. 539–541, vol. 341/.

*Primary Examiner*—Jeffrey Stucker
(74) *Attorney, Agent, or Firm*—Heller Ehrman White & McAuliffe, LLP

(57) ABSTRACT

The present invention relates to an immunodeficiency virus of drill monkeys, its RNA, the corresponding cDNA, proteins derived therefrom and fragments of the nucleic acids or proteins. The invention likewise relates to the diagnostic use of the nucleic acids and proteins mentioned and their fragments and to a diagnostic.

6 Claims, 9 Drawing Sheets

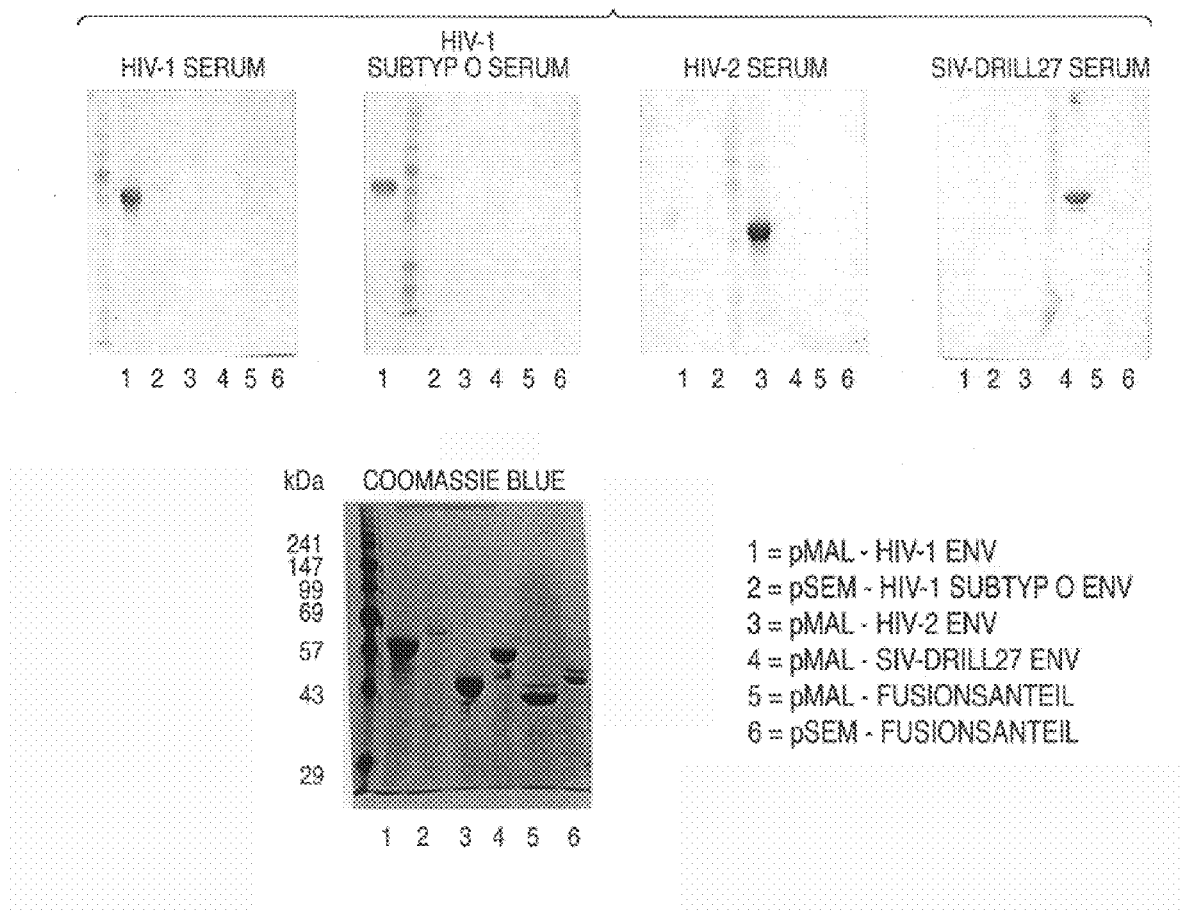

LENTIVIRUS FROM THE GROUP OF IMMUNODEFICIENCY VIRUSES OF DRILL MONKEYS (*MANDRILLUS LEUCOPHAEUS*) AND THEIR USE

The present invention relates to the immunodeficiency virus SIM27 of drill monkeys, whose RNA or a part thereof is complementary to the sequence shown below, and variants of this virus. Moreover, the viral RNA, the corresponding CDNA, proteins derived therefrom and fragments of the nucleic acids or proteins are a subject of the present invention. The invention likewise relates to the diagnostic use of the mentioned nucleic acids and proteins and their fragments, and a diagnostic comprising these nucleic acids and/or proteins and/or fragments thereof.

Primates have been developing for approximately 30 million years, which has lead to a high degree of variability of the individual primate species. The New World monkeys (Platyrrhini) are differentiated from the Old World monkeys (Catarrhini), which for their part are divided into the hominoids (Hominoidae) and the cercopithecoids (Cercopithecoidea). Together with the primates, various infective agents have also developed, which have adapted to the individual primate species or, for example, to a whole family. Examples of virus are the simian pathogenic and the human pathogenic herpesviruses, which although they can still infect individuals of another primate species, are naturally not transmitted from one primate species to the other. Other viruses still infect all primates, such as the rabies virus, the yellow fever virus and the filovirus.

Lentiviruses are subdivided into the genera of the spume viruses, the T-leukemia/lymphoma viruses and the immunodeficiency viruses. A general survey of the leukemia and immunodeficiency viruses of the monkeys and their pathogenicity is found in the article of Hayami (Hayami M et al., Curr. Top. Microbiol. Immunol. 1994; 188: 1–20). Spume viruses appear to occur only in monkeys. Since until now a pathogenicity of the spume viruses has not been detected, this virus is being less intensively investigated than HIV/SIV and HTLV/STLV.

HTLVs, the human T-leukemia viruses type I and type II, are structurally very similar to STLVs, the simian (monkey) T-lymphoma viruses (Franchini et al., AIDS Res Human Retrovirus 1994; 10: 1047–1060). Thus the difference in the virus species, STLV I and II, and the viruses between man (HTLV) and monkeys (STLV) is a sign of a long individual evolution in the individual primates, if a cross-transmission between the various primate species can be excluded (Franchini et al., AIDS Res Human Retrovirus 1994; 10: 1047–1060). STLV-infected monkeys occur over the entire world (Hayami M et al., Curr. Top. Microbiol. Immunol. 1994; 188: 1–20), whereas SIV-infected monkeys are only to be found naturally in Africa, which is an indication of the fact that SIV very probably developed later than STLV.

Molecular biology results show clearly that HIV-1 is very closely related to the immunodeficiency viruses of the chimpanzee. The latter viruses are subsequently designated as SIV-1, whereas the virus of the mangabeys, SIVsm, is designated as SIV-2. SIV-1 and HIV-1 derive with high probability from a precursor virus, just as SIV-2 and HIV-2 probably have a common precursor. Up to 25% of troops monkeys can naturally be infected with SIV-2 without signs of the virus pathogenesis being detectable in the infected animals (Chen Z et al., J Virol. 1996; 70: 3617–3627). In the case of SIV-2, infections in man were detected which do not differ in their pathogenesis from an HIV-2 infection. SIV-2 is closely related to HIV2 and particularly epidemically widespread in West Africa south of the Sahara, in the same region in which the mangabeys live (Gao FL et al., Nature 1992; 358: 495–499). The results of the investigations on SIV show that in addition to the SIV-2 (SIVsm) of mangabeys the immunodeficiency viruses of the African green meerkat represent a further type, perhaps SIV-3, and in addition meanwhile some further simian SIVs have been isolated which cannot be assigned to the groups of viruses mentioned and which probably represent the SIV type 4. This SIV-4 type is formed by the viruses of the Sykes monkeys (Cercopithecus mitis), the Hoest monkeys (Cercopithecus 1'hoesti) (Hirsch VM et al., J. Virol. 1999; 73: 1036–1045), the red cap mangabeys (Cercopithecus torquatus torquatus) (Georges-Courbot MC et al., J. Virol. 1998; 72: 600–608), the mandrill monkeys SIVmnd (Mandrillus sphinx) (Tsujimoto H et al., Nature 1989; 341: 539–541), and the drill monkeys (Mandrillus leucophaeus) (Clewley JP et al., J. Virol. 1998; 72: 10305–10309). All previously isolated SIV-4s can be cultured in human peripheral blood lymphocytes and some in the human permanent cell line Molt4 clone 8 (Hirsch VM et al., J. Virol. 1999; 73: 1036–1045), which indicates that the infection of man with these viruses should also be possible. The SIV-4 type is so different from the SIV-2 type that an SIVmac(SIV2)-specific p25 antigen test cannot detect SIVhoest (SIV4) produced in the supernatant of infected cells (Hirsch VM et al., J. Virol. 1999; 73: 1036–1045), as the Gag region is too divergent for recognition by monoclonal antibodies. The phylogenetic comparison of the nucleic acid sequences of the simian viruses also shows that the SIV-4 described here differs from SIV-2 and SIV-3 (Korber et al. Human Retroviruses and AIDS 1997. A compilation and analysis of nucleic acid and amino acid sequences. Los Alamos National Laboratory, New Mexico, 1998).

As described above, a virus similar to SIVcpz is possibly the precursor virus of viruses causing human HIV-1 infections, which the high similarity of viruses of the group HIV1-M, –N and –O to SIV-1 indicates.

To date, there are no reports that humans have been infected with SIV-4. A nosocomial infection with SIV-3 or SIV-2 occurred due to contamination of the eczematous skin of a laboratory assistant (Khabbaz RF et al., N. Engl. J. Med. 1994; 330: 172–177). The SIV replicated for a certain time which was sufficient for the induction of a strong antibody response, but was not sufficient to establish a permanent infection (Khabbaz RF et al., N. Engl. J. Med. 1994; 330: 172–177). About 3.5 years after seroconversion, the laboratory assistant appeared to be free of the infection (Khabbaz RF et al., N. Engl. J. Med. 1994; 330: 172–177). Whether this path of virus elimination is the rule or whether persistent infections with corresponding pathogenesis can also result from the infective event is unknown.

Since until now no epidemiological studies on target groups in central Africa have been carried out which can show whether variant viruses such as SIV-4 also circulate in the human population, infection of man cannot be confirmed, but can also not be excluded.

As was seen in the example of the HIV-1 subtype O, antibody detection tests on the basis of HIV-1 subtype M were not sufficiently reactive in order to be able to detect all subtype O-infected patients (Simon F et al. AIDS 1994; 8: 1628–1629). The diagnosis of an infection with an aberrant human pathogenic SIV subtype could probably also not be made, as it must be assumed that the ELISA exploratory tests based on HIV-1 and/or HIV-2 antigens are negative or would only be slightly reactive, and the attempt at confirmation by means of the immunoblot produced a negative or probably questionable result. The diagnosis could probably also not be made by means of the nucleic acid tests, since with the presently available tests, for example, neither the nucleic acid of the viruses of group O nor that of HIV-2 can be reliably amplified (Gürtler L et al., 12th World AIDS Conference Geneva Basic Science 1: 121–124).

The drill monkeys described here (*Mandrillus leucophaeus*) are animals which originate from the western region of Cameroon bordering Nigeria and live wild there in the bushland. Drill monkeys have become widespread in the central West-African region. The animals are hunted and eaten, which is why the stock in recent years has continuously decreased. Young animals are in some cases picked up and kept in the vicinity of the houses as pets. The monkey 27 described here (3 years old) was captured from a free hunting reserve and then domesticated over the course of a year and has had no contact with other monkeys of the same or of a similar species.

As described in Example 2, the virus originating from monkey 27 was replicated in human PBLs. Genomic DNA and thus also integrated proviral DNA of the SIV was isolated from the infected cells. The deciphering of the sequence of the total genome of the SIV is described in Example 3. The PCR (polymerase chain reaction) method was employed for the multiplication of the viral DNA. The components needed for carrying out the process can be acquired commercially.

Using this process, it is possible to amplify DNA sequences if DNA regions of the sequence to be amplified are known, or known sections are sufficiently similar. Short complementary DNA fragments (oligonucleotides=primers) which add to a short region of the nucleic acid sequence to be amplified must then be synthesized. For carrying out the test, nucleic acids are combined with the primers in a reaction mixture which additionally contains a polymerase and nucleotide triphosphates. The polymerization (DNA synthesis) is carried out for a specific time, then the nucleic acid strands are separated by warming. After cooling, the polymerization starts again.

The amplified genome sections were sequenced by the Sanger method. As described in Example 4, the genome of SIM27 was subjected to phylogenetic comparisons which showed that it is a strongly divergent novel simian immunodeficiency virus.

The present invention therefore relates to:

1.) Immunodeficiency viruses which branch off as a side branch from the SIM27 side branch after the branching of SIM27 in a phylogenetic investigation of their total genome on the nucleic acid plane, as is described in Example 4 (see FIG. 1)

2.) GAG proteins and fragments thereof which branch off as a side branch from the SIM27 side branch after the branching of SIM27 in a phylogenetic investigation of their total sequence on the amino acid plane, as is described in Example 4 (see FIG. 2).

3.) Pol proteins and fragments thereof which branch off as a side branch from the SIM27 side branch after the branching of SIM27 in a phylogenetic investigation of their total sequence on the amino acid plane, as is described in Example 4 (see FIG. 4), or a POL protein fragment or subfragments thereof which branch off as a side branch from the SIM27 side branch after the branching of SIM27 in the region of the sequence including this amino acid sequence, published by Clewley (Clewley JP et al., J. Virol. 1998; 72: 10305–10309), as has been investigated as described in Example 4 (see FIG. 6).

4.) ENV proteins and fragments thereof which branch off as a side branch from the SIM27 side branch after the branching of SIM27 in a phylogenetic investigation of their total sequence on the amino acid plane, as is described in Example 4 (see FIG. 7).

Of particular interest is furthermore the consideration of the strongly immunogenic cysteine loop region in the Erxv gene, which is therefore of particular diagnostic importance. The cysteine-loop regions of various immunodeficiency viruses are shown in Table 1 (SEQ ID NOS: 26–57, respectively).

TABLE 1

| | | | | |
|---|---|---|---|---|
| S1M27.ENV | | RLTALEEYVADQSRLAVWG | CSFSQVC | HTNVKW |
| SIV-Mandrill, | MNDGB1 | RLTSLENYIKDQALLSQWG | CSWAQVC | HTSVEW |
| HIV1-N, | YBF30 | KVLAIERYLRDQQILSLWG | CSGKTIC | YTTVPW |
| HIV1-C, | 96bw05.02 | RILAVERYLKDQQLLGIWG | CSGKLIC | TTAVPW |
| HIV1-O, | ANT70C | RLLALETLLQNQQLLSLWG | CKGKLVC | YTSVKW |
| SIV-CPZ, | CPZGAB | RLLAVERYLQDQQILGLWG | CSGKAVC | YTTVPW |
| HIV1-O, | MVP5180 | RLQALETLIQNQQRLNLWG | CKGKLIC | YTSVKW |
| SIV-1hoesti | | RLTALEEYVKHQALLASWG | CQWKQVC | HTNVEW |
| SIV-SYKES | | RLTALETYLRDQAILSNWG | CAFKQIC | HTAVTW |
| SIV-CPZ, CPZANT | | RMLAVEKYLRDQQLLSLWG | CADKVTC | HTTVPW |
| SIV-CPZ-US | | RVLAVERYLKDQQILGLWG | CSGKTIC | YTTVPW |
| HIV1-F, | 93br020.1 | RVLAVERYLKDQQLLGLWG | CSGKLIC | TTNVPW |
| HIV1-A, | 92ug037 | RVLAVERYLRDQQLLGIWG | CSGKLIC | PTNVPW |
| HIV1-H, | 90cr056 | RVLAVERYLRDQQLLGIWG | CSGKLIC | TTNVDW |
| HIV1-D, | NDK | RVLAVERYLRDQQLLGIWG | CSGRHIC | TTNVPW |
| HIV2-B, | UC1 | RVTAIEKYLKDQALLNSWG | CAFRQVC | HTTVPW |
| SIV-D, | MNE | RVTAIEKYLKDQAQLNAWG | CAFRQVC | HTTVPW |
| SIV-D, | MM239 | RVTAIEKYLKDQAQLNAWG | CAFRQVC | HTTVPW |
| SIV, | SME543 | RVTAIEKYLKDQAQLNSWG | CAFRQVC | HTTVPW |
| SIV-D, | SMM-PBJ-6P9 | RVTAIEKYLKDQAQLNSWG | CAFRQVC | HTTVPW |
| SIV-D, | STM | RVTAIEKYLKDQAQLNSWG | CAFRQVC | HTTVPW |
| HIV2-A, | CAM2 | RVTAIEKYLKDQAQLNSWG | CAFRQVC | HTTVPW |
| HIV2-A, | GH1 | RVTAIEKYLKDQAQLNSWG | CAFRQVC | HTTVPW |
| HIV2-B, | EHO | RVTAIEKYLKDQAQLNSWG | CAFRQVC | HTTVPW |
| SIV-SMM, | PGM | RVTAIEKYRKDQAQLNSWG | CAFRQVC | HTTVPW |
| SIV-VERVET, | AGM155 | RVTALEKYLADQARLNAWG | CAWKQVC | HTTVPW |
| SIV-VERVET, | AGM3 | RVTALEKYLEDQARLNAWG | CAWKQVC | HTTVPW |
| SIV-SABAEUS, | AGMSAB1 | RVTALEKYLEDQARLNIWG | CAFRQVC | HTTVLW |
| SIV-VERVET, | AGMTY6 | RVTALEKYLEDQARLNSWG | CAWKQVC | HTTVEW |
| SIV-GRIVET, | AGM677A | RVTALEKYLEDQARLNSWG | CAWKQVC | HTTVPW |
| SIV-VERVET, | REV | RVTALEKYLEDQARLNVWG | CAWKQVC | HTTVPW |
| SIV-TANTALUS, | TAN1 | RVTALEKYLEDQTRLNLWG | CAFKQVC | HTTVPW |

As can be clearly seen, either lysine or arginine occurs in position 3 of the cysteine loop (C12345C) in nearly all representatives of immunodeficiency viruses. The only exception up to now was found in the immunodeficiency virus MNDGB1, which was likewise isolated from a drill monkey (Mandrillus spinx). With great probability it is to be assumed from this that antibodies formed against this modified epitope cannot be recognized or can be recognized with clearly decreased efficiency from diagnostic tests known up to now which are based on the customary arginine- or lysine-containing antigens.

This invention therefore likewise relates to antigens in which arginine and/or lysine within the cysteine loop region in position 3 has been replaced by any desired amino acid, particularly preferably a polar amino acid such as serine or an amino acid having an aliphatic side chain such as alanine.

The present invention is moreover described in the examples and in the patent claims, where the examples serve for summarization and no restriction of the present invention must be derived therefrom.

EXAMPLE 1

Identification of the SIM27 infection in drill monkeys

In the course of a study, EDTA blood was taken from drill monkeys in the villages of rural Cameroon, in which they were kept, and this was analyzed in various HIV tests. On testing the serum of the monkey SIM27 for antibodies, a competitive ELISA for HIV-1 was negative and an ELISA from Dade Behring (Enzygnost HIV-1/2 plus) recognizing HIV-1, −2 and −O was likewise negative, the extinction lying near the threshold value. In the analysis of the HIV-1 Western blot (virus MVP899-87) which was carried out at the same time, no virus-specific bands were to be seen, in the HIV-2 blot (virus MVP11971-87), the band gp36 was to be seen strongly, and the bands p55 and p68 were to be seen, and in the HIV-1 group O blot (virus MVP5180-91), the bands p24 and p55 were to be seen. Gp36 is the transmembrane protein of HIV-2, the bands p55 and p68 correspond to the reverse transcriptase (p55) plus the RNaseH (p68) of HIV-2, and p24 is the inner core protein of HIV-1 group O viruses and p55 the precursor protein of gag and thus also p24. 20 ml of plasma from the animals were employed in order to develop the Western blot. According to the analysis of the nucleic acid sequence, the virus MVP11971-87 is a representative of the group HIV-2A, the virus MVP899 a representative of HIV-1B.

The SIV infection of the monkeys with the drill virus is thus distinguished:

- by negativity in normal screening ELISAs for HIV antibodies,
- by serological cross reaction in the env and pol region with the HIV-2 transmembrane glycoprotein and the reverse transcriptase in the Western blot,
- by serological cross reaction in the gag region with the inner core protein of HIV-1 group O and absent cross reaction with the core proteins of group M (HIV-1B) in the Western blot.

EXAMPLE 2

Isolation of the SIM27 Virus

The lymphocyte fraction was isolated by Ficoll gradient centrifugation from 5 ml each of EDTA blood of the monkeys. The lymphocytes were stimulated with PHA (phytohemaglutinih, 5 mg/ml) and PMA (myristylphorbol ester, 10 ng/ml), after 3 days both additives were washed out and the culture was continued in the presence of RPMI-1640, as usual, with interleukin-2 addition. The PMA stimulation was described by Kubo et al. (Kubo M et al., J. Virol 1997; 71: 7560–7566).

The culture conditions were similar to those which have been described by Tamalet et al. (Tamalet, C. et al., AIDS 1994; 1083–1088). After one week in culture, human PHA-stimulated and nonstimulated blood lymphocytes (PBLs) were added to the monkey lymphocytes and the addition was repeated once weekly until it was possible after about 3 weeks to detect beginning SIV production by means of a commercially obtainable p24 antigen test (Abbott, Wiesbaden).

The virus was then subcultured on human lymphocytes from the supernatant of the cells. All attempts to transfer the SIM27 to permanent culture cells such as HUT-78 or Jurkat have failed up to now. By means of monthly subculturing, it was possible to keep SIM27 on PBL in culture for 9 months from then on.

EXAMPLE 3

DNA Isolation, Amplification and Structural Characterization of Genome Sections of the HIV Isolate SIM27

Genomic DNA from SIM27-infected blood lymphocytes was isolated by standard methods (Current Protocols in Molecular Biology, Wiley Interscience, 1994).

The total genome was amplified exclusively by means of PCR (polymerase chain reaction). All PCRs were begun by means of "Hot Start": after addition of all components of the PCR, except the polymerase, this was added only after heating the sample to 94° C., which strongly reduces the extension of nonspecifically binding primers.

A general survey of the individual stages of the deciphering of the genome is shown in FIG. 8.

For the characterization of genome regions of the isolate SIM27, PCR experiments were carried out with primer pairs from the region of the integrase in the pol gene. The PCR (Saiki et al., Science 239: 487–491, 1988) was modified as follows:

For the first amplification of HIV-specific DNA regions, 5 μl (200 μg/ml) of genomic DNA from SIM27-infected blood lymphocytes were pipetted into a 50 μl reaction mixture (0.25 mM dNTP, 1 μM each primer, 10 mM tris HCl, pH 8.3, 50 mM KCl, 1.5 mM MgCl2, 0.001% gelatin, 2.5 units platinum-Taq DNA polymerase (Gibco)) and amplified according to the following temperature program:

1) initial denaturation: 3 min. 95° C.,
2) amplification: 30 sec. 94° C., 30 sec. 49° C., 30 sec. 68° C. (30 cycles).

The primers used for the PCR had the following sequence:

(Seq. ID No. 1 and 2)

5'3'

5pol2380agm GCC ATG TGT CCA AAA TGT CA

3pol2930agm CTT CTC TGT AGT AGA CTC TA

5 μl of the amplificate were employed as a template for a second nested PCR with the following primers and the same temperature profile:

(Seq. ID No. 3 and 4)

5pol2460agm TAG TAG CAG TCC MYR KWG (M=A/C,Y=C/T,R=A/G,K=G/T,W=A/T)

3pol2760agm TCT CTA ATT TGT CCT ATG AT

The amplificate thus obtained was sequenced directly without cloning.

The sequence found is shown in Table 2.

TABLE 2

(SEQ ID NO: 17):

```
  1  AGTAGCAGTC CATGTAGCCA GTGGATACCT AGAGGCAGAA GTAATACCAG
 51  CAGAGACAGG AAAAGAGACA GCACATTTCC TGTTAAAGTT AGCAGGCAGG
101  TGGCCTGTAA AACATTTACA CACTGACAAT GGCCCCAACT TTGTCAGTGA
151  AAAGGTAGCC ACAGTCTGTT GGTGGGCTCA AATAGAGCAC ACCACAGGTG
201  TACCCTATAA CCCCCAGAGT CAGGGAGTAG TGGAAGCAAA GAATCATCAT
251  CTTAAGACAA TCATAGGACA AATTAGAGA
```

Based on the publication of Clewley (Clewley JP et al., J. Virol 1998; 72: 10305–10309), a further amplificate was obtained in the 5' region of the pol gene. The primers DR1, DR2 and, for the nested PCR, DR4 and DR5 described by Clewley were used, as well as the temperature cycles described in this publication. The polymerases used were DNA-Taq polymerase (Perkin Elmer) and the buffers described above.

The sequence according to Table 3 was obtained here:

TABLE 3

(SEQ ID NO: 18):

```
  1  GGGATTCCGC ANCCGGCAGG TCTAAAACAA TGTGAACAGA TCACAGTATT
 51  GGATATAGGA GATGCCTATT TTTCATGCCC ATTGGATGAG GACTTTAGAA
101  AGTATACTGC ATTCACCATT CCATCGGTGA ATAATCAGGG GCCCAGGAAT
151  CAGATACCAG TATAATGTCC TCCCNCAGGG NTGGAAGGGG TCCCC
```

In a next amplification, the region of SIM27 lying between the amplificates already obtained was amplified. The primers mentioned below were used here.

For the first PCR:

(Seq. ID No. 5 and 6)

1216 ATG CCC ATT GGA TGA GGA C

1197 GAC TGT GGC TAC CTT TTC ACT

For the nested PCR:

(Seq. ID No. 7 and 8)

1218 CAT CGG TGA ATA ATC AGG

1226 GGT ATT ACT TCT GCC TCT A

The platinum-Taq DNA polymerase (Gibco) was used according to the following temperature program:

1) initial denaturation: 2 min. 95° C., 2) amplification: 30 sec. 95° C., 30 sec. 55° C., 150 sec. 68° C. (30 cycles).

The sequence according to Table 4 was obtained here.

The region of the total sequence of the 5'-LTR region of the genome up to the pol gene was amplified with the following primer pairs:

1. PCR:

(Seq. ID No. 9 and 10)

1248 CTC AAT AAA GCT TGC CTT GA

1217 GTC CTC ATC CAA TGG GCA T

2. Nested PCR:

10 (Seq. ID No. 11 and 12)

1249 TRD CTA GAG ATC CCT CAG A (R=A/, D=G/A/T)

1219 CCA ATA CTG TGA TCT GTT CAC platinum-Taq DNA polymerase (Gibco) was in each used according to the following temperature program:

1) initial denaturation: 2 min. 95° C., 2) amplification: 30 sec. 95° C., 30 sec. 50° C., 180 sec. 68° C. (30 cycles). 1×enhancer (Gibco) was used in addition to the buffers indicated above.

The sequence according to Table 5 was obtained here:

TABLE 4

(SEQ ID NO: 19):

```
  1  CATCGGTGAA TAATCAGGGC CCAGGAATCA GATACCAGTA TAATGTCCTC
 51  CCACAGGGAT GGAAAGGCTC TCCAGCAATT TTTCAGGCAA CAGCTGATAA
101  AATCTTGAAA ACATTCAAAG AAGAATACCA GAGGTATTAA TTTATCAGTA
151  TATGGATGAT CTGTTCGTGG GAAGTGACTT AAATGCCACT GAACATAACA
201  AAATGATAAA CAAGTTGAGA GAGCATCTGA GATTCTGGGG GCTCGAGACC
251  CCAGATAAGA AGTTTCAAAA GGAACCTCCT TTTGAATGGA TGGGATATGT
301  GCTACACCCA AAGAAATGGA CAGTGCAGAA AATACAACTA CCAGAAAAAG
351  AGCAATGGAC AGTGAATGAT ATTCAGAAAT TGGTAGGAAA ACTTAATTGG
401  GCAAGTCAGA TATATTCCGG AATTAAAACA AAAGAGCTCT GTAAATTGAT
451  CAGAGGAGCA AAACCTCTAG ATGAAATAGT AGAATGGACA AGAGAAGCAG
501  AATTAGAGTA TGAAGAGAAT AAGATAATAG TGCAGGAGGA GGTGCATGGA
551  GTGTACTATC AGCCAGAAAA ACCACTGATG GCAAAAGTAC AAAAGTTGAC
```

TABLE 5

(SEQ ID NO: 20):

```
  1  TRDCTAGAGA TCCCTCAGAT TTGTGCCAGA CTTCTGATAT CTAGTGAGAG
 51  TAGAGAAAAA TCTCCAGCAG TGGCGCCCGA ACAGGGACTT GACGAAGAGC
101  CAAGTCATTC CCACCTGTGA GGGACAGCGG CGGCAGCCRG CCGGACCGAC
151  CCACCCGGTG AAGTGAGTTA ACCAAGGAGC CCCGACGCGC AGGACACAAG
201  GTAAGCGGTG CACCGTGCTG TAGTGAGTGT GTGTCCAGGA TCCGCTTGAG
251  CAGGCGAGAT CGCCGAGGCA ACCCCAGTAG AAAAAGAAAA GAGGGGAAGT
301  AAGGCCGAGG CAAAGTGAAA GTAAAAGAGA TCCTCTGAGA AGAGGAACAG
351  GGGGCAATAA AATTGGCGCG AGCGCGTCAG GACTTAGGGG AAGAGAATTG
401  GATGAGCTGG AAAAGATTAG GTTACGGCCC TCCGGAAAGA AAAAATACCA
451  GCTAAAACAT GTGATATGGG TAAGCAAGGA ACTAGATAGA TTTGGCCTAC
501  ATGAAAAGTT GTTAGAAACC AAGGAAGGAT GCGAAAAAAT TCTTAGCGTA
551  CTCTTTCCTC TAGTTCCTAC AGGGTCAGAA AATTTAATTT CGCTGTACAA
601  CACCTGCTGT TGCATTTGGT GCGTACATGC GAAAGTGAAA GTAGCAGATA
651  CAGAAGAGGC AAAAGAGAAA GTAATACAAT GCTACCATCT AGTGGTTGAA
701  AAACAGAATG CAGCCTCAGA AAAAGAAAAA GGAGCAACAG TGACACCTAG
751  TGGCCACTCA ARAAATTACC CCATTCAGAT AGTAAATCAA ACCCCAGTAC
```

The still missing region of the total sequence of the integrase up to the 3'-LTR was amplified with the following primer pairs, the primer 1270 being discarded on account of the sequence of the 5' LTR region (prior amplificate):

1. PCR:
   (Seq. ID No. 13 and 14)
   1246 CCT ATT CAT GGC CAG GTA
   1270 GAT TTT TCT CTA CTC TCA CTA
2. Nested PCR:
   (Seq. ID No. 15 and 16)
   1196 AGT GAA AAG GTA GCC ACA GTC
   12710 GAT TTT TCT CTA CTC TCA CTA The platinum-Taq DNA polymerase (Gibco) was in each case used according to the following temperature program:
1) initial denaturation: 2 min. 95° C.,
2) amplification: 30 sec. 95° C., 30 sec. (47° C. 1.PCR; 51° C. 2. PCR), 360 sec. 68° C. (30 cycles). 1×enhancer (Gibco) was used in addition to the buffers indicated above.

The sequence according to Table 6 was obtained here:

TABLE 6

(SEQ ID NO: 21):

```
   1  AGTGAAAAGG TAGCCACAGT CTGTTGGTGG GCTCAAATAG AGCACACCAC
  51  AGGTGTACCC TATAACCCCC AGAGTCAGGG AGTAGTGGAA GCAAAGAATC
 101  ATCATCTTAA GACAATCATA GAACAAGTTA GGGATCAAGC AGAAAAATTA
 151  GAAACAGCAG TACAAATGGC AGTATTAATA CACAATTTTA AAAGAAAAGG
 201  GGGGATAGGG GAGTATAGTC CAGGAGAAAG AATAGTAGAT ATCATAACCA
 251  CAGACATTCT AACAACTAAA TTACAACAAA ATATTTCAAA AATTCAAAAT
 301  TTTCGGGTTT ATTACAGAGA AGGAAGGGAT CAACAGTGGA AAGGACCAGC
 351  AGAACTCATT TGGAAAGGAG AAGGCGCTGT GGTGATTAAA GAACGGACAG
 401  ACTTAAAGGT GGTACCAAGA AGAAAAGCCA AAATCATCAG AGATTATGGA
 451  AAAGCAGTGG ATAGTAATTC CCACATGGAG AGTAGAGAGG AATCAGCTTG
 501  AGAAATGGAA TTCATTAGTA AAATATCATA AATATAGGGG AGAAAAATAC
 551  CTAGAAAGAT GGGAACTATA CCACCATTTC CAATGCTCGG GGTGGTGGAC
 601  ACACTCTAGA AAAGATGTTT ACTTTAAAGA TGGCTCAGTA ATAAGCATTA
 651  CTGCCTTCTG GAATCTTACC CCAGAGAAAG GATGGTTGTC TCAATATGCA
 701  GTTACAATAG AATATGTAAA AGAAAGCTAT TATACTTACA TAGACCCAGT
 751  TACAGCAGAC AGAATGATTC ATTGGGAATA TTTCCCATGT TTTACAGCCC
 801  AGGCTGTGAG AAAAGTACTG TTTGGAGAAA GACTAATAGC TTGCTACAGC
 851  CCCTGGGGAC ACAAAGGACA GGTAGGGACT CTACAATTCC TGGCTTTGCA
 901  AGCTTACCTT CAGTATTGTA AACATGGCAG AAAGAGCACC AGAAGTGCCG
 951  GAAGGGGCAG GAGAGATACC TCTAGAACAG TGGCTAGAAA GATCATTAGA
1001  ACAACTCAAC AGAGAGGCCC GGTTACACTT CCACCCAGAG TTCCTTTTCC
1051  GTCTTTGGAA CACTTGTGTA GAACATTGGC ATGATAGACA CCAGAGGAGC
1101  CTGGAGTATG CAAAATACAG ATATCTTTTG TTGGTGCATA AGGCCATGTT
1151  TACCCATATG CAACAGGGAT GCCCATGTAG AAATGGGCAC CCAAGAGGAC
1201  CTCCTCCTCC AGGATTGGCC TAATTTCTGT CTTGCAGATG GAACAGCCAC
1251  CTGAGGACGA GGCTCCACAG AGAGAACCTT ATAATGAATG GCTGATAGAT
1301  ACCTTGGCAG AAATCCAGGA GAAGCTTTG AAGCATTTTG ATAGGCGCTT
```

The total sequence which results from the sum of the sequences according to Tables 2 to 6 is shown in Table 7:

TABLE 7

(SEQ ID NO: 22):

```
   1 TRDCTAGAGA TCCCTCAGAT TTGTGCCAGA CTTCTGATAT CTAGTGAGAG
  51 TAGAGAAAAA TCTCCAGCAG TGGCGCCCGA ACAGGGACTT GACGAAGAGC
 101 CAAGTCATTC CCACCTGTGA GGGACAGCGG CGGCAGCCGG CCGGACCGAC
 151 CCACCCGGTG AAGTGAGTTA ACCAAGGAGC CCCGACGCGC AGGACACAAG
 201 GTAAGCGGTG CACCGTGCTG TAGTGAGTGT GTGTCCAGGA TCCGCTTGAG
 251 CAGGCGAGAT CGCCGAGGCA ACCCCAGTAG AAAAAGAAAA GAGGGGAAGT
 301 AAGGCCGAGG CAAAGTGAAA GTAAAAGAGA TCCTCTGAGA AGAGGAACAG
 351 GGGGCAATAA AATTGGCGCG AGCGCGTCAG GACTTAGGGG AAGAGAATTG
 401 GATGAGCTGG AAAAGATTAG GTTACGGCCC TCCGGAAAGA AAAAATACCA
 451 GCTAAAACAT GTGATATGGG TAAGCAAGGA ACTAGATAGA TTTGGCCTAC
 501 ATGAAAAGTT GTTAGAAACC AAGGAAGGAT GCGAAAAAAT TCTTAGCGTA
 551 CTCTTTCCTC TAGTTCCTAC AGGGTCAGAA AATTTAATTT CGCTGTACAA
 601 CACCTGCTGT TGCATTTGGT GCGTACATGC GAAAGTGAAA GTAGCAGATA
 651 CAGAAGAGGC AAAAGAGAAA GTAAAACAAT GCTACCATCT AGTGGTTGAA
 701 AAACAGAATG CAGCCTCAGA AAAAGAAAAA GGAGCAACAG TGACACCTAG
 751 TGGCCACTCA AGAAATTACC CCATTCAGAT AGTAAATCAA ACCCCAGTAC
 801 ACCAGGGAAT TTCTCCCAGA ACACTGAATG CTTGGGTAAA ATGTATAGAG
 851 GAGAAGAAAT TCAGCCCAGA AATAGTGCCT ATGTTCATAG CTTTGTCAGA
 901 AGGATGCCTC CCATACGACC TCAACGGCAT GCTCAATGCC ATTGGGGACC
 951 ATCAGGGAGC TCTCCAAATA GTGAAAGATG TCATCAATGA CGAAGCTGCA
1001 GACTGGGATC TTAGACATCC TCAGATGGGG CCTATGCCCC AAGGGGTGCT
1051 AAGAAACCCA ACAGGGAGTG ACATAGCAGG AACCACCAGC AGCATAGAAG
1101 AACAAATTGA ATGGACAACT AGGCAGCAAG ATCAGGTAAA TGTAGGAGGA
1151 ATTTACAAAC AATGGATAGT TCTGGGATTG CAAAAATGTG TGAGCATGTA
```

In 3 reading frames, the nucleotide sequence was converted into amino acid sequences, after which the amino acid sequences of GAG (Table 8), POL (Table 9) and ENV (Table 10) were identified by homology comparisons.

TABLE 8

GAG (SEQ ID NO: 23):

```
  1 IGASASGLRG RELD'LEKIR LRDSGKKKYQ LKHVIWVSKE LDRFGLHLKL
 51 LETKEGCEKI LSVLFPLVPT GSENLISLYN TCCCIWCVHA KVKVADTEEA
101 KEKVKQCYHL VVEKQNAASE KEKGATVTPS GHSRNYPIQI VNQTPVHQGI
151 SPRTLNAWVK CIEEKKFSPE IVPMFIALSE GCLDYDLNGM LNAIGDHQGA
201 LQIVKDVIND EAADWDLRHP QMGPMPQGVL RNPTGSDIAG TTSSIEEQIE
251 WTTRQQDQVN VGGIYKQWIV LGLQKCVSMY NPVNILDIKQ GPKEPFKDYV
301 DRFYKALRAE RTDPQVKNWM TQTLLIQNAN PDCK.AILKGL GMNPTLEEML
351 LACQGVGGPK YKAQMMAEAM QEVQGKIM.MQ ASGGPPRGPP RQPPRNPRCP
401 NCGKFGHVLR DCRAPRKRGC FKCGDPGHLM RNCPKMVNFL GNAPWGSGKP
451 RNFPAVPLTP TAPPMPGLED PAEKMLLDYM KKGQQMKAER EAKREKDKGP
501 YEAAYNSLSS LFGTDQLQ
```

TABLE 9

POL (SEQ ID NO: 24):

```
  1 FFRECSLGQW QTQELSCRAT DPNGTPDARI RGPSREDATG LHELGATDEG
 51 REGSQTGEGQ RPLRGGLQLP QFSLWNRPTT VVEIEGQKVE ALLDTGADDT
101 VIKDLQLTGN WKPQIIGGIG GAIRVKQYFN CKITVAGKST HAJVLVGPTP
151 VNIIGRNVLK KLGCTLNFPI SKIETVKVTL KPGTDGPRIK QWPLSKEKIL
201 ALQEICNQME KEGKISRIGP ENPYNTPVFC IKKKDGASWR KLVDFRQLNK
251 VTQDFCEVQL GIPHPGGLKQ CFQITVLDIG GAYFSCPLDE CFRKYTAFTI
301 PSVNNQGPGI RYQYNVLPQG WKGSPAIFQA TADKILKTFK EEYPEVLIYQ
351 YMDDLFVGSD LNATEHNKMI NKLREHLRFW GLETPDKKGQ KEPPFEWMGY
901 VLHPKKWTVQ KTQLPEKEQW TVNDIQKLVG KLNWASQIYS GIKTKELCKL
451 IRGAKPLDEI VEWTREAELE YEENKIIVQE EVHGVYYQPFE KPLMAKVQKL
```

TABLE 10

ENV (SEQ ID NO: 25):

```
 1 QWVTVYYGTP KWHPARTHLF CATDNNSFWV TTSCVPSLLH YEEQHIPNIT
51 ENFTGPITEN EVIRQAWGAI SSMIDAVLKP CVKLTPYCVK MKCTKGDTDT
```

TABLE 10-continued

ENV (SEQ ID NO: 25):

```
101 TERTTSTTSS WSTSTPTSTP MTPNTTGLDI DSNNTEPTTQ ENRICKFNTT
151 GLCRDCRLEI EENFRYQDIT CRNSSEDTEE CYMTHCNSSV ITQDCNKAST
201 DKMTFRLCAP PGYVLLRCRE KLNQTKLCGN ITAVQCTDPM PATISTMFGF
251 NGTKHDYDEL ILTNPQKINE FHDHKYVYRV DKKWKLQVVC RRKGNRSIIS
301 TPSATGLLFY HGLEPGKNLK KGMCQLKGLW GKAMHQLSEE LRKINGSIYR
351 KWNETAGCRK LNKQNGTGCS LKTIEVSEYT TEGDPGAETI MLLCGGEYFF
401 CNWTKIWKTW NNQTSNVWYP WMSCNIRQIV DDWHKVGKKI YMPPASGFNN
451 EIRCTNDVTE MFFEVQKKEE NKYLIKFIPQ DEIQNQYTAV GAHYKLVKVD
501 PIGFAPTDVH RYHLPDVKQK RGAVLLGMLC LLGLAGSAMG SVAIALTVQS
551 QALLNGIVEQ QKVLLSLIDQ HSELLKLTIW GVKNLQARLT ALEEYVADQS
641 RLAVWGCSFS QVC HTNVKWP NDSIVPNWTS ETWLEWDKRV TAITTTNMTID
651 LQRAYELEQK NMFELQKLGD LTSWASWFDL TWWFKYIKIG ILIIVIIGL
701 RILACLWSVL GRFRQGYRPL PYVFKGDYHR PHNLKQPDKE RGEEQDREKQ
751 NISSENYRPG SGRAWSKEQV ETWWKESRLY IWLKSTQAVI EYGWQELKAA
801 GAEIYKILQS AAQRLWSGGH QLGLSCIRRA TAFGRGVRNI PRRIRQGAEV
851 LLN
```

EXAMPLE 4

Determination of the Phylogenetic Position of SIM27

Selection of the sequences:

From the HIV WWW server of the LANL (Los Alamos National Laboratory, hiv-web.lanl.gov), 31 HIV and SIV sequences were selected which all comprised complete SIV genomes and representatives of the various HIV-1 and HIV-2 subtypes. The following sequences according to Table 11 were taken into consideration.

TABLE 11

| Genbank | |
|---|---|
| Accession No.: | Name: |
| AF075269 | SIV-1'hoesti |
| AF077017 | SIV-SMM, PGM |
| L06042 | SIV-SYKES |
| M27470 | SIV-Mandrill, MNDGB1 |
| L40990 | SIV-VERVET, REV |
| M29975 | SIV-VERVET, AGM155 |
| M30931 | SIV-VERVET, AGM3 |
| X07805 | SIV-VERVET, AGMTY6 |
| M66437 | SIV-GRIVET, AGMG77A |
| U04005 | SIV-SABAEUS, AGMSAB1 |
| AF103818 | SIV-CPZ-US |
| U42720 | SIV-CPZ, CPZANT |
| X52154 | SIV-CPZ, CPZGAB |
| U58991 | SIV-TANTALUS, TAN1 |
| U72748 | SIV, SME543 |
| Y00277 | SIV-D, MAC250 |
| M32741 | SIV-D, MNE |
| M33262 | SIV-D, MM239 |
| L09213 | SIV-D, SMM-PBJ-6P9 |
| M80194 | SIV-D, SMM9 |
| M83293 | IV-D, STM |
| U51190 | HIV1-A, 92ug037 |
| AF110967 | HIV1-C, 96bw05.02 |
| M27323 | HIV1-D, NDK |
| AF005494 | HIV1-F, 93br020.1 |
| AF005496 | HIV1-H, 90cr056 |
| AJ006022 | HIV1-N, YBF30 |
| L20587 | HIV1-O, ANT70C |
| L20571 | HIV1-O, MVP5180 |
| D00835 | HIV2-A, CAM2 |
| M30895 | HIV2-A, GH1 |
| U27200 | HIV2-B, EHO |
| L07625 | HIV2-B, UC1 |

With the aid of the Genbank accession numbers of these sequences, the actual sequence entries were extracted from the gene database "Genbank". With the aid of annotation, the genes env, gag and pol were extracted from these sequences and translated into the amino acid sequence. For the translation, only those sequences were used which were annotated as functional. Pseudogenes and genome sections not annotated as one of the 3 genes were not taken into consideration.

In addition, the sequence of the genome of SIM27 was compared with the actual gene database "Genbank" in order not to overlook an SIV partial sequence having a high relationship to SIM27. 2 partial sequences of SIVrcm (gag and pol) and a pol partial sequence of Mandrillus leucophaeus (Clewley JP et al., J. Virol. 1998; 72: 10305–10309) were identified as additionally relevant here:

| | |
|---|---|
| RCM-GAG | SIV, RCM gag |
| RCM-POL | SIV, RCM pol |
| CLEW-POL | SIV, Drill, Clewley |

In total, 4 data sets were obtained in this way: 3 protein data sets (env, gag and pol), and one from genomic sequences (GENOME).

Alignment:

The above sequences were aligned together with the corresponding SIM27 sequences using CLUSTALW (Version 1.74) with standard settings (Thompson J. D et al., Nucleic Acids Res. 22: 4673–4680 (1994)). The sequence alignments thus obtained were then checked manually.

The published pol partial sequence of drill monkeys (Clewley et al.), and the pol partial sequence of the RCM monkey was added once more each to the pol sequence alignment in analyses which were separate in each case. The same was carried out for the GAG partial sequence of the RCM monkeys for the gag alignment.

For the addition of the individual sequences to the alignments, the profile alignment option of CLUSTALW 1.74 was used with standard settings.

3 further protein data sets with small partial sequences RCM-GAG, RCM-POL and DRILL-POL thus resulted. Each of these data sets was considered only with respect to the region of the respective partial sequence.

Phylogenetic Analyses

Using the above seven alignments (GENOME (FIG. 1), GAG (FIG. 2), RCM-GAG (FIG. 3), POL (FIG. 4), RCM-POL (FIG. 5), DRILL-POL (FIG. 6), ENV (FIG. 7)), phylogenetic family trees were then independently set up. For this, the neighbor-joining method, as is implemented in CLUSTALW 1.74, was used in 1000 boot strap analyses. To calculate the trees, the standard settings were used, only all alignment gaps with holes were ignored, and the correction for multiple mutations was switched on.

EXAMPLE 5

Detection of the Diagnostic Relevance in the Western Blot

According to known methods of molecular biology (Current Protocols in Molecular Biology, Wiley Interscience, 1994), the region of env containing the cysteine loop was stably expressed either as a fusion with the maltose-binding protein (pMAL-New England Biolabs) or as a fusion with β-Gal (Knapp et al., Biotechniques, Vol. 8, No. 3, 1990). The proteins were blotted on nitrocellulose, incubated overnight with the sera in a dilution of 1:100 in TBS containing 5% skimmed milk (150 mM NaCl, 50 mM tris pH 8.0), washed with TBS and incubated with anti-human IgG-AP (Sigma A064) and anti-monkey IgG-AP (Sigma A1929) for 2 h in a dilution of 1:1000 and stained according to the manufacturer's instructions by means of Nitrotetrazolium Blue (Sigma N-6878) and 5-bromo-4-chloroindolyl phosphate.p-toluidine (Bachem M105). The results shown in Table 9 were obtained (FIG. 9).

TABLE 9

| Protein/serum | Anti-HIV1 serum | Anti-HIV1 -subtype O serum | Anti-HIV2 serum | Anti-SIV- drill 7 serum |
|---|---|---|---|---|
| PMAL-HIV1env | +++ | ++ | − | − |
| PSEM-HIV1- subtype-O-env | ++ | ++ | − | − |
| pMAL-HIV2-env | − | − | +++ | − |
| pMAL-SIM27- env | − | − | − | +++ |
| pMAL | − | − | − | − |
| PSEM | − | − | − | − |

It was surprisingly seen here that the env region of SIM27 does not react with anti-HIV-1, anti-HIV-1 subtype O and anti-HIV2 sera and at the same time antibodies from SIM27, which react strongly with SIM27-env, could not be detected by the use of HIV-1-env, HIV-1-subtype O env and HIV2-env. It is therefore to be assumed from this that in the case in which SIM27 or a variant with comparable serological properties ought to complete the transition into the human population, the detection of antibodies against SIM27 in human sera is not possible with the tests currently employed, but rather SIM27-env, or antigens derived therefrom having comparable immunological properties, have to be employed.

BRIEF DESCRIPTION OF THE FIGURES

FIG. 9 Western blot, as described in Example 5.

ABBREVIATIONS

Figure 1:
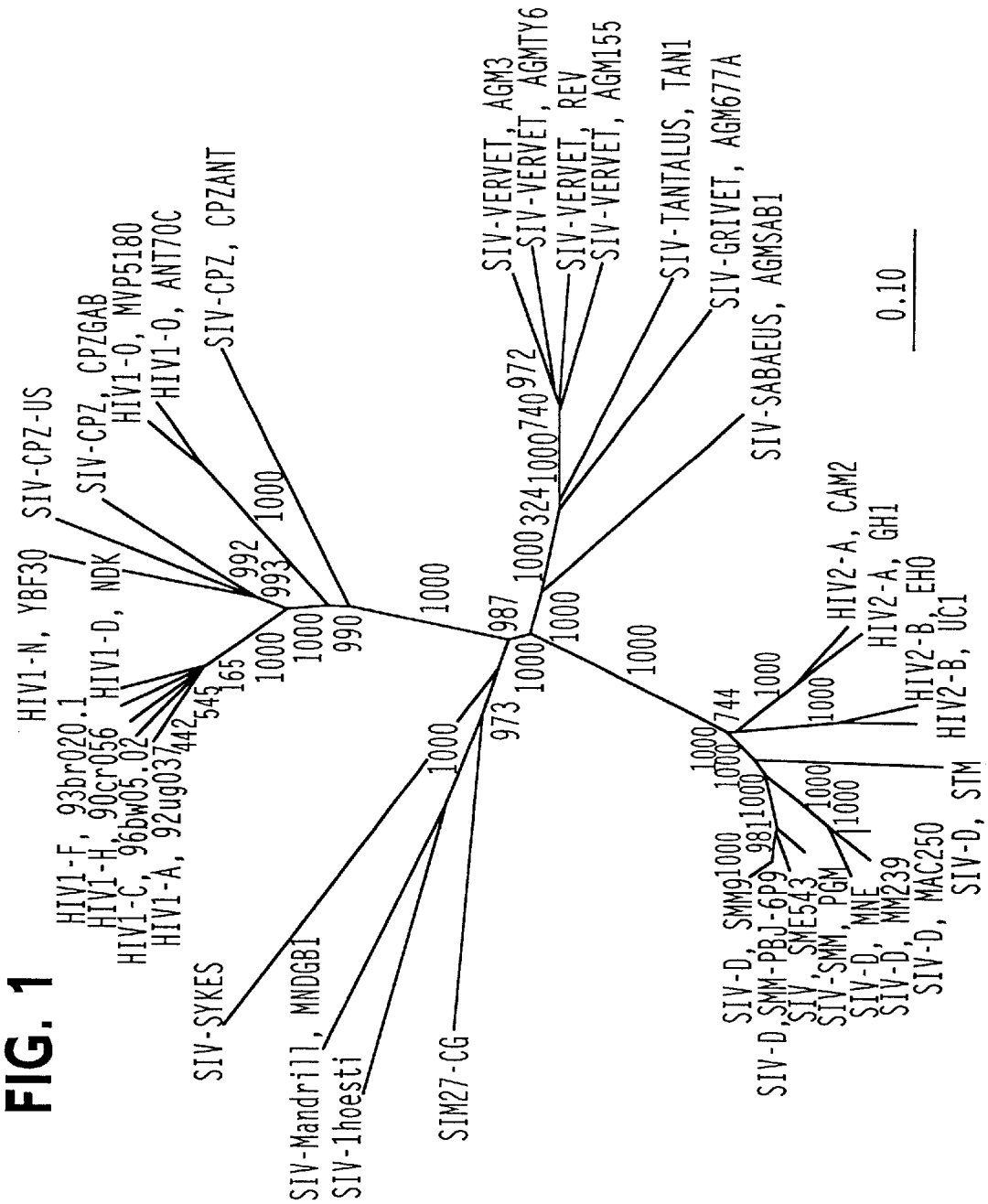
FIG. 1 Phylogenetic investigation of the sequences of Table 11 including the total genome of SIM27 as described in Example 4 by the multiple alignment and the neighbor-joining method of ClustalW Version 1.74
Figure 2:
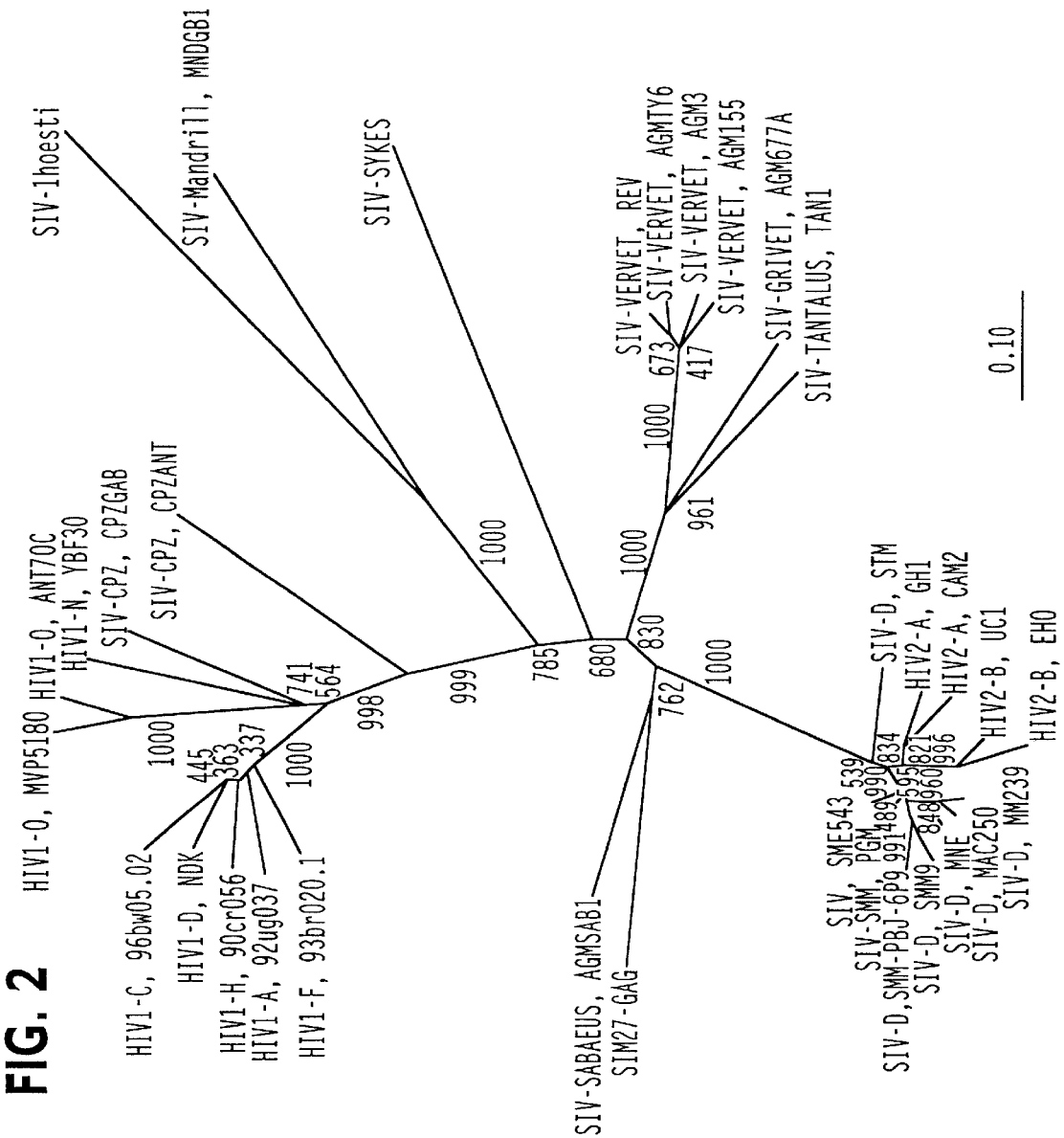
FIG. 2 Phylogenetic investigation of the GAG proteins extracted from the sequences of Table 11 including the GAG protein of SIM27 (Table 8) as described in Example 4 by the multiple alignment and the neighbor-joining method of ClustalW Version 1.74
Figure 3:
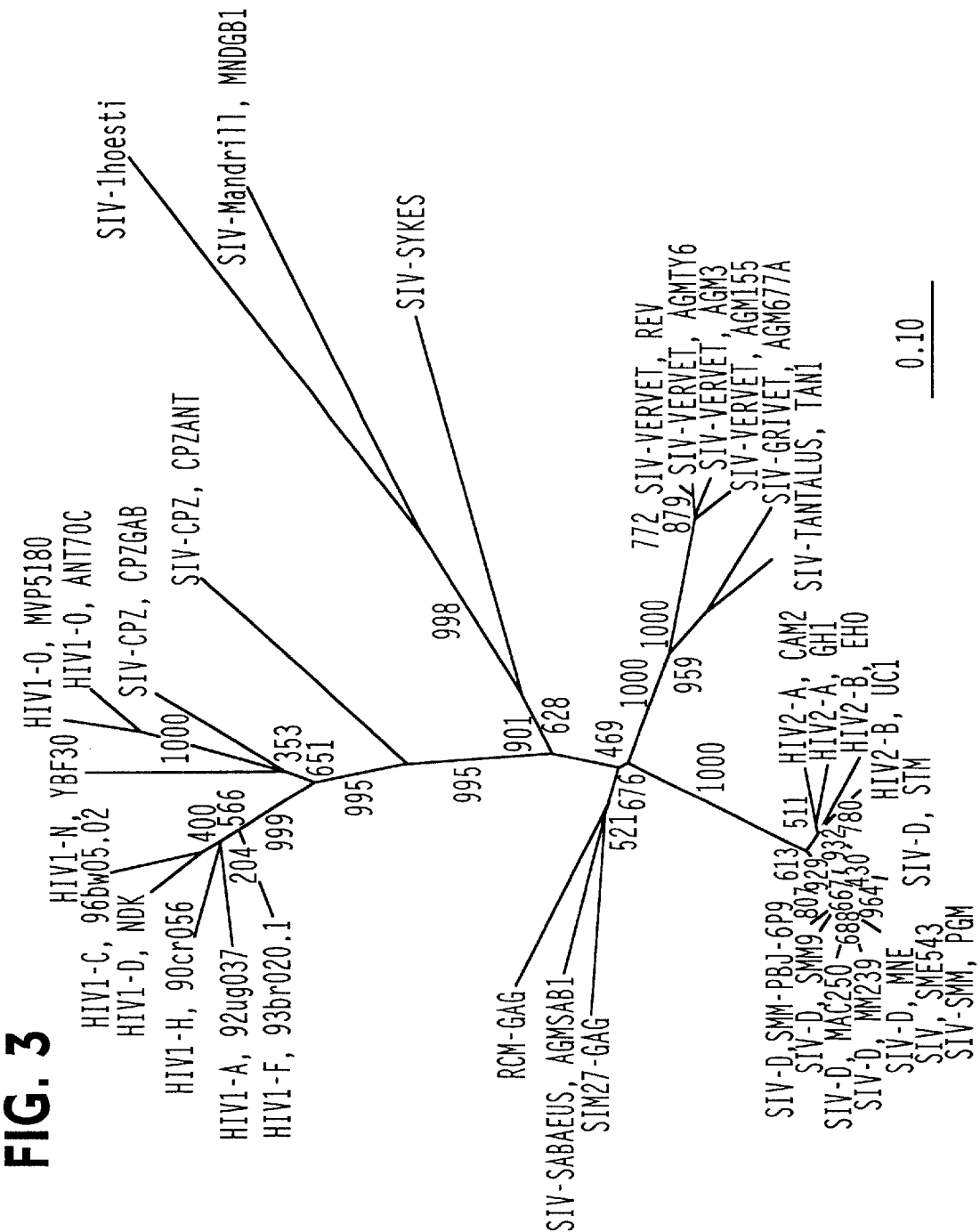
FIG. 3 Phylogenetic investigation of the GAG proteins extracted from the sequences of Table 11 including the GAG protein of SIM27 (Table 8) and the GAG partial sequence of SIVrcm as described in Example 4 by the multiple alignment and the neighbor-joining method of ClustalW Version 1.74
Figure 4:
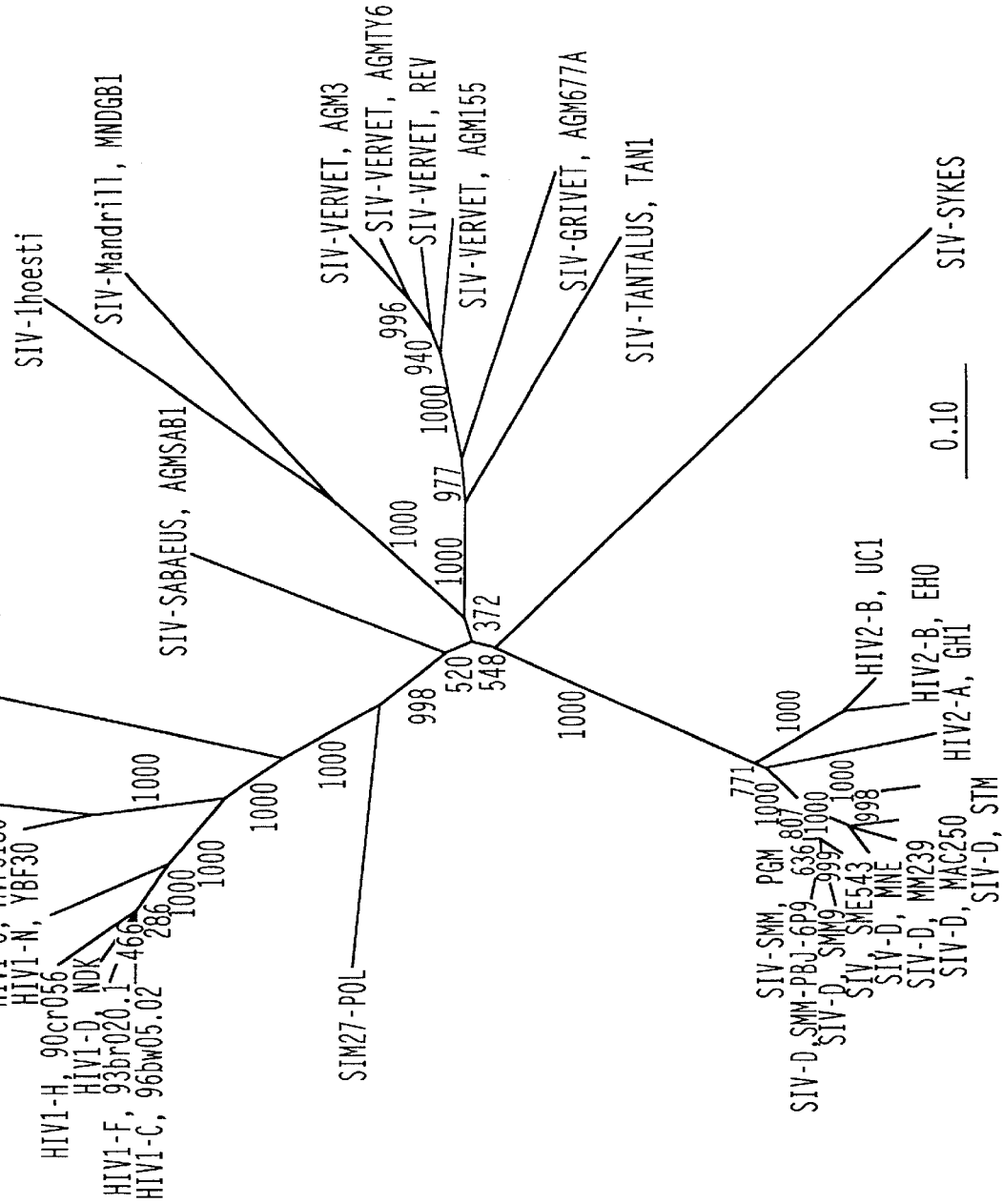
FIG. 4 Phylogenetic investigation of the POL proteins extracted from the sequences of Table 11 including the POL protein of SIM27 (Table 9) as described in Example 4 by the multiple alignment and the neighbor-joining method of ClustalW Version 1.74
Figure 5:
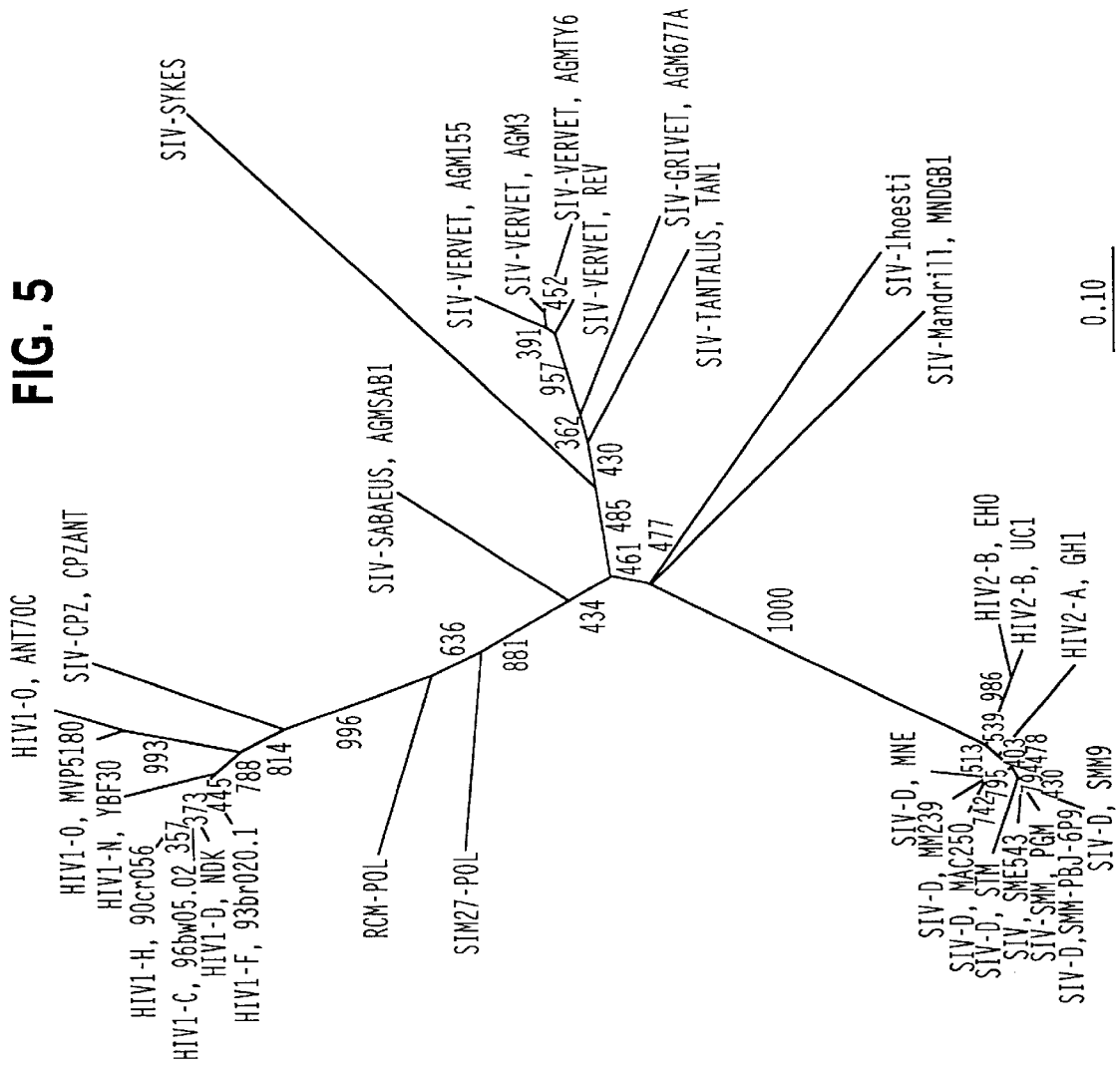
FIG. 5 Phylogenetic investigation of the POL proteins extracted from the sequences of Table 11 including the POL protein of SIM27 (Table 9) and the POL partial sequence of SIVrcm as described in Example 4 by the multiple alignment and the neighbor-joining method of ClustalW Version 1.74
Figure 6:
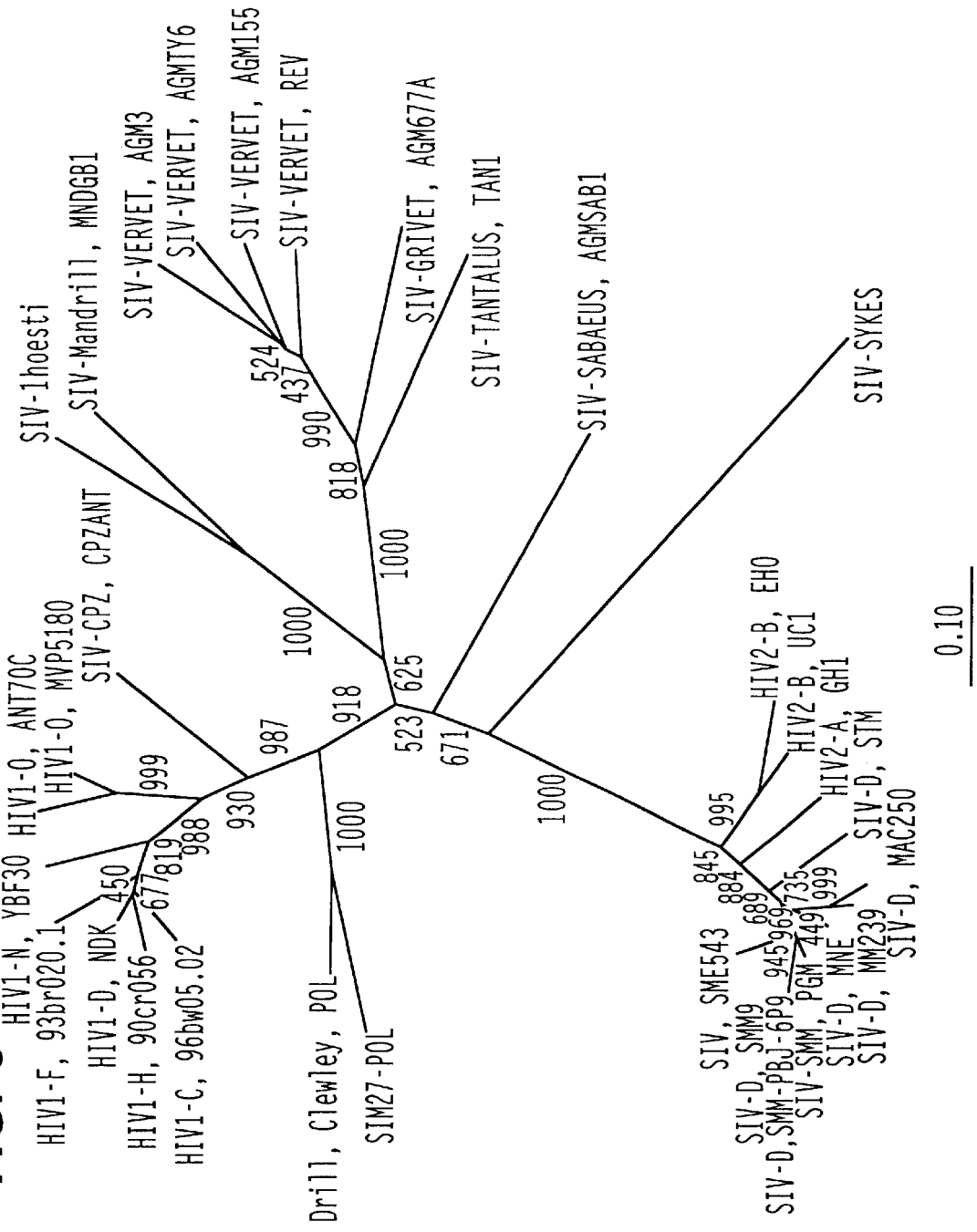
FIG. 6 Phylogenetic investigation of the POL proteins extracted from the sequences of Table 11 including the POL protein of SIM27 (Table 9) and the POL partial sequence as published by Clewley (Clewley JP et al., J. Virol. 1998; 72: 10305–10309) and as described in Example 4 by the multiple alignment and the neighbor-joining method of ClustalW Version 1.74
Figure 7:
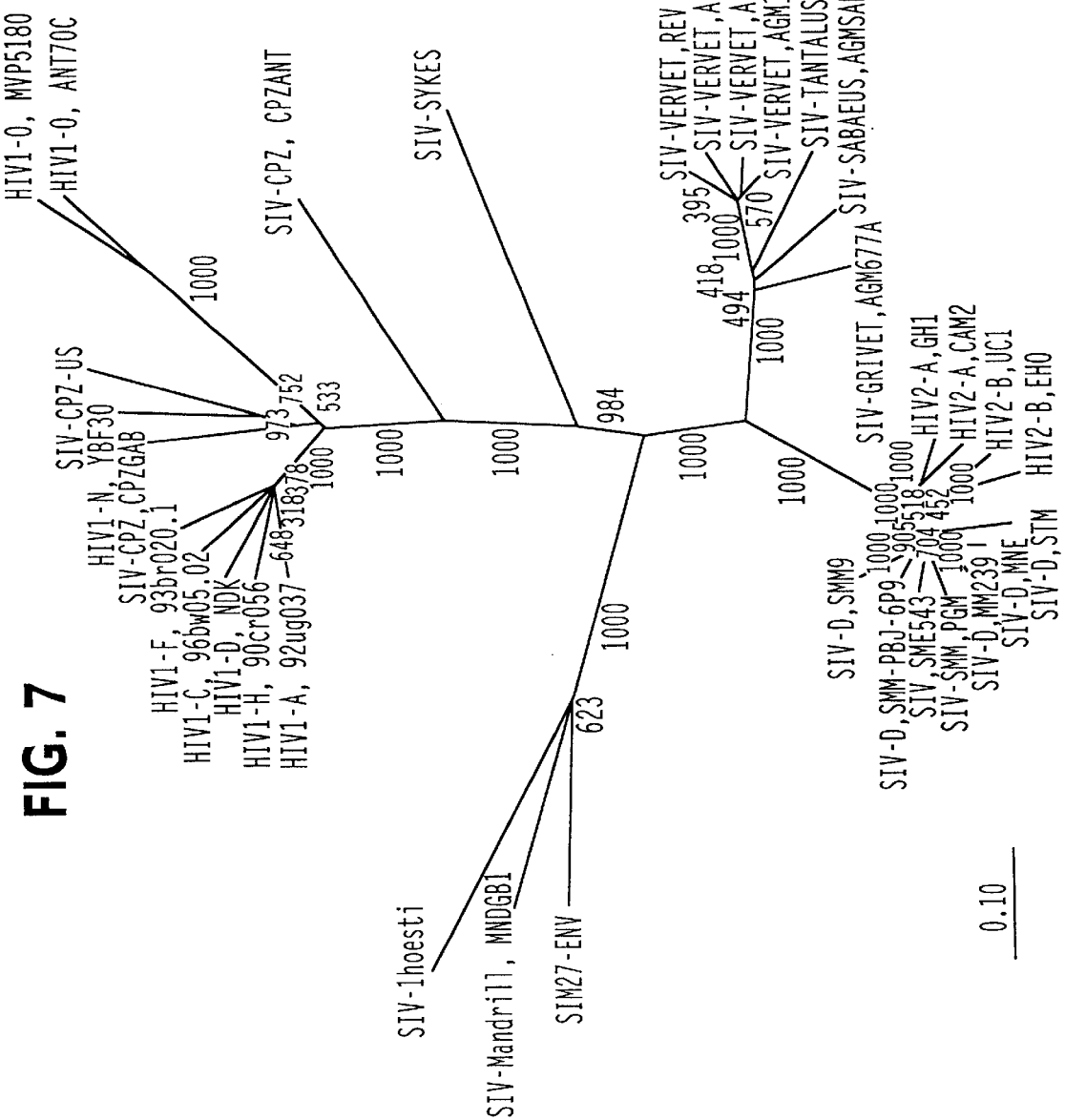
FIG. 7 Phylogenetic investigation of the ENV proteins extracted from the sequences of Table 11 including the ENV protein of SIM27 (Table 10) as described in Example 4 by the multiple alignment and the neighbor-joining method of ClustalW Version 1.74
Figure 8:
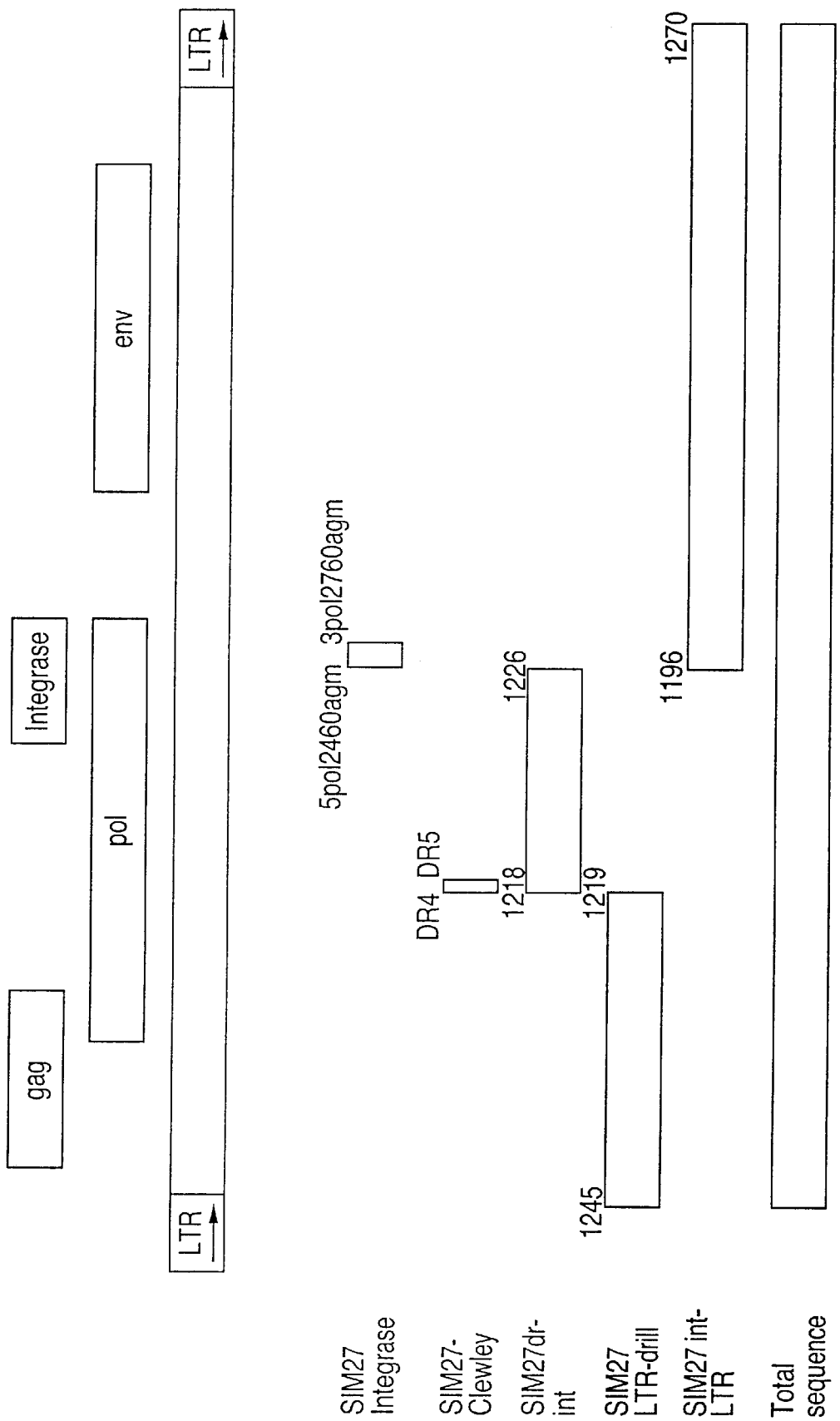
FIG. 8 General survey of the individual PCR amplifications which lead to the complete genomic nucleic acid sequence of SIM27.

| | |
|---|---|
| HIV: | Human immunodeficiency virus |
| SIV: | Simian (monkey) immunodeficiency virus |
| HTLV: | Human T-lymphoma virus |
| STLV: | Simian T-lymphoma virus |
| p: | Protein |
| gp: | Glycoprotein |
| pol: | Gene of the enzymes of HIV or SIV, designated according to the polymerase |
| gag: | Gene of the core proteins of HIV or SIV |
| env: | Gene of the surface glycoproteins/glyco- proteins of HIV or SIV |
| IN: | Integrase |
| RT: | Reverse transcriptase |
| PR: | Protease |

What is claimed is:

1. An isolated and purified nucleic acid molecule comprising SEQ ID NO: 21.

2. An isolated immunodeficiency virus comprising SEQ ID NO: 21.

3. The virus of claim 2, further comprising a nucleic acid molecule selected from the group consisting of SEQ ID NO: 17, SEQ ID NO: 18, SEQ ID NO: 19, SEQ ID NO; 20 and SEQ ID NO: 22.

4. An isolated immunodeficiency virus comprising SEQ ID NO: 21 or a variant thereof, wherein said variant encodes SEQ ID NO: 26, wherein the arginine or lysine in position 3 is substituted with a different amino acid.

5. An isolated immunodeficiency virus of claim 4, wherein said different amino acid is a polar amino acid or an amino acid having an aliphatic side chain.

6. The isolated immunodeficiency virus of claim 5, wherein said polar amino acid is serine and said amino acid having an aliphatic side chain is alanine.

* * * * *

SEQUENCE LISTING

```
<160> NUMBER OF SEQ ID NOS: 57

<210> SEQ ID NO 1
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 1
gccatgtgtc caaaatgtca                                               20

<210> SEQ ID NO 2
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 2
cttctctgta gtagactcta                                               20

<210> SEQ ID NO 3
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 3
tagtagcagt ccmyrkwg                                                 18

<210> SEQ ID NO 4
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 4
tctctaattt gtcctatgat                                               20

<210> SEQ ID NO 5
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 5
atgcccattg gatgaggac                                                19

<210> SEQ ID NO 6
<211> LENGTH: 21
<212> TYPE: DNA
<213> ORGANISM: Unknown
```

```
<220> FEATURE:
<221> NAME/KEY: misc_feature
<222> LOCATION: ()..()
<223> OTHER INFORMATION: primer, non-genomic DNA

<400> SEQUENCE: 6
gactgtggct accttttcac t                                              21

<210> SEQ ID NO 7
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 7
catcggtgaa taatcagg                                                  18

<210> SEQ ID NO 8
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 8
ggtattactt ctgcctcta                                                 19

<210> SEQ ID NO 9
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 9
ctcaataaag cttgccttga                                                20

<210> SEQ ID NO 10
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 10
gtcctcatcc aatgggcat                                                 19

<210> SEQ ID NO 11
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 11
trdctagaga tccctcaga                                                 19
```

<210> SEQ ID NO 12
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 12
ccaatactgt gatctgttca c                                               21

<210> SEQ ID NO 13
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 13
cctattcatg gccaggta                                                   18

<210> SEQ ID NO 14
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 14
gatttttctc tactctcact a                                               21

<210> SEQ ID NO 15
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 15
agtgaaaagg tagccacagt c                                               21

<210> SEQ ID NO 16
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer, non-genomic DNA

<400> SEQUENCE: 16
gatttttctc tactctcact a                                               21

<210> SEQ ID NO 17
<211> LENGTH: 279
<212> TYPE: DNA
<213> ORGANISM: SIV - viral

<400> SEQUENCE: 17
agtagcagtc catgtagcca gtggatacct agaggcagaa gtaataccag cagagacagg     60

```
aaaagagaca gcacatttcc tgttaaagtt agcaggcagg tggcctgtaa aacatttaca    120
cactgacaat ggccccaact ttgtcagtga aaggtagcc acagtctgtt ggtgggctca    180
aatagagcac accacaggtg taccctataa cccccagagt cagggagtag tggaagcaaa    240
gaatcatcat cttaagacaa tcataggaca aattagaga                           279
```

<210> SEQ ID NO 18
<211> LENGTH: 195
<212> TYPE: DNA
<213> ORGANISM: SIV - viral
<220> FEATURE:
<221> NAME/KEY: Unsure
<222> LOCATION: (175)..(175)
<223> OTHER INFORMATION: "n" can be any base
<221> NAME/KEY: Unsure
<222> LOCATION: (181)..(181)
<223> OTHER INFORMATION: "n" can be any base

<400> SEQUENCE: 18

```
gggattccgc anccggcagg tctaaaacaa tgtgaacaga tcacagtatt ggatatagga    60
gatgcctatt tttcatgccc attggatgag gactttagaa agtatactgc attcaccatt   120
ccatcggtga ataatcaggg gcccaggaat cagataccag tataatgtcc tcccncaggg   180
ntggaagggg tcccc                                                     195
```

<210> SEQ ID NO 19
<211> LENGTH: 1551
<212> TYPE: DNA
<213> ORGANISM: SIV - viral

<400> SEQUENCE: 19

```
catcggtgaa taatcagggc ccaggaatca gataccagta taatgtcctc ccacagggat     60 ggaaggctc tccagcaatt tttcaggcaa cagctgataa atcttgaaa acattcaaag    120 aagaatacca gaggtattaa tttatcagta tatggatgat ctgttcgtgg aagtgactt   180 aaatgccact gaacataaca aaatgataaa caagttgaga gagcatctga gattctgggg   240
gctcgagacc ccagataaga gtttcaaaa ggaacctcct tttgaatgga tgggatatgt   300
gctacaccca agaaatgga cagtgcagaa atacaacta ccagaaaaag agcaatggac   360
agtgaatgat attcagaaat tggtaggaaa acttaattgg gcaagtcaga tatattccgg   420
aattaaaaca aaagagctct gtaaattgat cagaggagca aaacctctag atgaaatagt   480
agaatggaca agagaagcag aattagagta tgaagagaat aagataatag tgcaggagga   540
ggtgcatgga gtgtactatc agccagaaaa accactgatg gcaaaagtac aaaagttgac   600
acaaggacag tggagttatc aaatagagca agaagaaac aaacctctca aggcaggaaa   660
atatgccagg acaaagaatg cccacacaaa tgagttaagg acacttgcag ggttagtaca   720
aaaaatagcc aaggaatgca tagtaatctg ggaagattg ccaaaatttt acctccccctt   780 ggagagagaa gtatgggatc aatggtggca tgattattgg caggtaacat ggatcccaga   840
gtgggaattc atctcaacac caccattgat aaggctatgg tacaacctcc tgaaagaacc   900
aattccagga gaagatgtat actatgtaga tgggggcagct aacagaaatt ctaaagaagg   960
caaggcagga tactatacag caaggggcaa aagtaaggta tagctttag aaaatacaac  1020 caatcagaag gcagagctga aggcaataga attagcccta aaagattcag gaccaagagt  1080
aaacatagta acagattcac agtatgcatt aggcatactc acagcatccc cagatcagtc  1140 agataaccc atagttaggg aaataattaa cctcatgata gccaaggaag cagtctacct  1200
```

| | | | | |
|---|---|---|---|---|
| gtcatgggta | ccagcccaca | agggtatagg | aggtaacgaa | caaatagaca aattagtaag | 1260 |
| ccaaggaatt | aggcaagtac | tattcctgga | aggaatagac | agagctcagg aagaacacga | 1320 |
| caaatatcat | aacaactgga | gagctttagc | tcaggaattc | agcatacctc ctatagtggc | 1380 |
| aaaagagata | gttgcacaat | gcccaaaatg | ccagataaaa | ggggaaccta ttcatggcca | 1440 |
| ggtagatgca | agtcctggga | catggcaaat | ggattgcacc | catctagaag gaaaggtcat | 1500 |
| catagtggca | gtccatgtag | ccagtggata | cctagaggca | gaagtaatac c | 1551 |

<210> SEQ ID NO 20
<211> LENGTH: 2500
<212> TYPE: DNA
<213> ORGANISM: SIV - viral

<400> SEQUENCE: 20

| | | | | |
|---|---|---|---|---|
| trdctagaga | tccctcagat | ttgtgccaga | cttctgatat | ctagtgagag tagagaaaaa | 60 |
| tctccagcag | tggcgcccga | acagggactt | gacgaagagc | caagtcattc ccacctgtga | 120 |
| gggacagcgc | cggcagccrg | ccggaccgac | ccacccggtg | aagtgagtta accaaggagc | 180 |
| cccgacgcgc | aggacacaag | gtaagcggtg | caccgtgctg | tagtgagtgt gtgtccagga | 240 |
| tccgcttgag | caggcgagat | cgccgaggca | accccagtag | aaaagaaaaa gaggggaagt | 300 |
| aaggccgagg | caaagtgaaa | gtaaaagaga | tcctctgaga | gaggaacag ggggcaataa | 360 |
| aattggcgcg | agcgcgtcag | gacttagggg | aagagaattg | gatgagctgg aaaagattag | 420 |
| gttacggccc | tccggaaaga | aaaatacca | gctaaaacat | gtgatatggg taagcaagga | 480 |
| actagataga | tttggcctac | atgaaaagtt | gttagaaacc | aaggaaggat gcgaaaaaat | 540 |
| tcttagcgta | ctctttcctc | tagttcctac | agggtcagaa | aatttaattt cgctgtacaa | 600 |
| cacctgctgt | tgcatttggt | gcgtacatgc | gaaagtgaaa | gtagcagata cagaagaggc | 660 |
| aaaagagaaa | gtaaracaat | gctaccatct | agtggttgaa | aaacagaatg cagcctcaga | 720 |
| aaaagaaaaa | ggagcaacag | tgacacctag | tggccactca | araaattacc ccattcagat | 780 |
| agtaaatcaa | accccagtac | accagggaat | ttctcccaga | acactgaatg cttgggtaaa | 840 |
| atgtatagag | gagaagaaat | tcagcccaga | aatagtgcct | atgttcatag ctttgtcaga | 900 |
| aggatgcctc | ccatacgacc | tcaacggcat | gctcaatgcc | attggggacc atcagggagc | 960 |
| tctccaaata | gtgaaagatg | tcatcaatga | cgaagctgca | gactgggatc ttagacatcc | 1020 |
| tcagatgggg | cctatgcccc | aagggggtgct | aagaaaccca | acaggagtg acatagcagg | 1080 |
| aaccaccagc | agcatagaag | aacaaattga | atggacaact | aggcagcaag atcaggtaaa | 1140 |
| tgtaggagga | atttacaaac | aatggatagt | tctgggattg | caaaaatgtg tgagcatgta | 1200 |
| caatccagtg | aatattctag | atataaaaca | gggaccaaaa | gaacccttta aggactatgt | 1260 |
| ggatcgattt | tacaaagctc | tgcgggcgga | gcgaacagat | ccacaagtga aaactggat | 1320 |
| gacgcagaca | ttgctcatcc | agaatgcaaa | cccagattgt | aaagccattc ttaagggatt | 1380 |
| aggcatgaac | cccaccttgg | aagaaatgtt | attggcatgt | caaggagtag ggggaccaaa | 1440 |
| gtataaagct | caaatgatgg | cagaagcaat | gcaggaggtg | caaggaaaaa ttatgatgca | 1500 |
| agcctcggga | ggaccaccgc | gggtcccccc | aaggcagcca | cccagaaatc ctagatgccc | 1560 |
| caactgtgga | aagtttggac | atgtactgag | agactgtaga | gccccaagaa agcgaggatg | 1620 |
| cttcaagtgt | ggagatccag | gacatctgat | gagaaactgc | ccaaagatgg tgaatttttt | 1680 |
| agggaatgct | ccytggggca | gtggcaaacc | caggaacttt | cctgccgtgc cactgacccc | 1740 |

-continued

| | |
|---|---|
| aacggcaccc ccgatgccag gattagagga yccagcagag argatgctrc tggattacat | 1800 |
| gaagaagggg caacagatga aggcagagag ggaagccaaa cgggagaagg acaaaggccc | 1860 |
| ttacgaggcg gcttacaact ccctcagttc tctctttgga acagaccaac tacagtagta | 1920 |
| gagatagagg ggcaaaaagt ggaggcccta ctagatacag gagcagatga cacagtaatc | 1980 |
| aaagatttac aattaacagg caattggaaa ccacaaatca taggaggaat tggaggagca | 2040 |
| attagggtaa agcaatattt caattgtaaa ataacagtgg caggtaaaag cactcatgct | 2100 |
| tcagtactag tgggccccac tcctgtaaat attataggta gaaatgtact taaaaagtta | 2160 |
| ggatgtactt tgaactttcc tattagtaar atagaaacag taaaggtaac actaaaacca | 2220 |
| ggaactgatg gaccaagaat caaacagtgg ccactgtcta agaaaagat tttagcctta | 2280 |
| caagaaatat gcaatcagat ggaaaagaa ggcaaaatct ctagaatagg tccagaaaat | 2340 |
| ccttacaaca caccagtgtt ttgtataaaa aagaaagatg gagccagctg gagaaaactg | 2400 |
| gtagatttta gacaattgaa taaagtgaca caggatttct ttgaggtgca gctaggaatc | 2460 |
| ccacatcctg gaggtctaaa acaatgtgaa cagatcacag | 2500 |

<210> SEQ ID NO 21
<211> LENGTH: 5428
<212> TYPE: DNA
<213> ORGANISM: SIV - viral

<400> SEQUENCE: 21

| | |
|---|---|
| agtgaaaagg tagccacagt ctgttggtgg gctcaaatag agcacaccac aggtgtaccc | 60 |
| tataaccccc agagtcaggg agtagtggaa gcaaagaatc atcatcttaa gacaatcata | 120 |
| gaacaagtta gggatcaagc agaaaaatta gaaacagcag tacaaatggc agtattaata | 180 |
| cacaattta aagaaaagg ggggataggg gagtatagtc caggagaaag aatagtagat | 240 |
| atcataacca cagacattct aacaactaaa ttacaacaaa atatttcaaa aattcaaaat | 300 |
| tttcgggttt attacagaga aggaagggat caacagtgga aaggaccagc agaactcatt | 360 |
| tggaaaggag aaggcgctgt ggtgattaaa gaagggacaa cttaaaggt ggtaccaaga | 420 |
| agaaaagcca aaatcatcag agattatgga aaagcagtgg atagtaattc ccacatggag | 480 |
| agtagagagg aatcagcttg agaaatggaa ttcattagta aaatatcata atatagggg | 540 |
| agaaaaatac ctagaaagat gggaactata ccaccatttc caatgctcgg ggtggtggac | 600 |
| acactctaga aaagatgttt actttaaaga tggctcagta ataagcatta ctgccttctg | 660 |
| gaatcttacc ccagagaaag gatggttgtc tcaatatgca gttacaatag aatatgtaaa | 720 |
| agaaagctat tatacttaca tagacccagt tacagcagac agaatgattc attgggaata | 780 |
| tttcccatgt tttacagccc aggctgtgag aaaagtactg tttggagaaa gactaatagc | 840 |
| ttgctacagc ccctggggac acaaaggaca ggtagggact ctacaattcc tggctttgca | 900 |
| agcttacctt cagtattgta aacatggcag aaagagcacc agaagtgccg gaaggggcag | 960 |
| gagagatacc tctagaacag tggctagaaa gatcattaga acaactcaac agagaggccc | 1020 |
| ggttacactt ccacccagag ttccttttcc gtctttggaa cacttgtgta gaacattggc | 1080 |
| atgatagaca ccagaggagc ctggagtatg caaaatacag atatctttg ttggtgcata | 1140 |
| aggccatgtt tacccatatg caacagggat gcccatgtag aaatgggcac ccaagaggac | 1200 |
| ctcctcctcc aggattggcc taatttctgt cttgcagatg gaacagccac ctgaggacga | 1260 |
| ggctccacag agagaacctt ataatgaatg gctgatagat accttggcag aaatccagga | 1320 |
| agaagctttg aagcattttg ataggcgctt gctacatgca gtaggctcat gggtgtatga | 1380 |

-continued

```
gcaacaggga gacaccttag aaggtgtcca aaagctaata actattctac aaagagcttt    1440
gtttttgcac ttcaggcatg gatgcaggga agccgcatt  ggacaagcag gagggaaata    1500
taattccctc agatcctttc caaggccaga caaccccttg taataaatgc tattgtaaaa    1560
gatgttgcta tcactgccag ttatgcttct tgcagaaagc cttagggata cattatcatg    1620
tctacagagt caggagacct cgacagagat ttttgggcga agtaccacca catagtgcag    1680
caactgtgga aagtaagta  aaagtaagt  agacatgctt agatatatag ttttaggaat    1740
agtcatagga ttagggatag gacaccaatg ggttacagtg tattatggaa cacctaaatg    1800
gcacccagct aggacacatc tcttttgtgc aacagataat aattccttt  gggtcacaac    1860 aagttgtgtg cccagcctat tgcactatga agaacaacac attcccaaca taacagaaaa    1920
cttcacaggc cccataacag agaatgaagt aataagacaa gcatggggag ctatctcttc    1980
catgatagat gcagtcttaa accctgtgt  aaagctgaca ccatattgtg tcaagatgaa    2040
atgcacaaag ggagatactg atactacaga aaggacaaca tcaaccactt cctcttggtc    2100
cacatccacc ccaacctcta cccctatgac tcccaatacc actggattag atatagactc    2160
aaacaataca gaacccacaa cacaagagaa tcggatatgt aaatttaata ctacaggatt    2220
atgtagagac tgcagattgg aaatagaaga aaacttcaga tatcaggata taacatgtag    2280
aaatagtagt gaagatactg aagagtgcta tatgacacat tgtaactcat cagtaataac    2340
acaggattgc aataaggcat caacagataa aatgactttt aggttgtgtg caccaccagg    2400
atatgtcctg ttgagatgta gagaaaagct aaaccaaacc aaattgtgtg gcaatattac    2460
agcagtgcaa tgcactgacc caatgcctgc aactatatcc actatgtttg gatttaatgg    2520
gaccaaacat gactatgatg agctaatttt aacaaaccct caaagataa  atgagtttca    2580 tgatcacaag tatgtatata gagttgataa aaaatggaag ctacaggtag tatgtagaag    2640
aaaagggaat agatcaataa tatcaacgcc aagtgctacg ggcttattgt tctatcatgg    2700
gctagaacca gggaaaaatt taaaaaaggg gatgtgccag ctgaagggat tatggggaaa    2760
ggccatgcac caactatcag aggaacttag aaagataaat ggaagtattt atagaaaatg    2820
gaatgagaca gcaggctgca gaaagctaaa caaacagaac ggtacaggtt gctcattgaa    2880
aacaatagaa gttagtgagt acaccacgga gggcgatccg ggggcagaga caattatgct    2940
tctttgtgga ggtgagtatt tcttttgtaa ttggacaaag atttggaaga catgaataa     3000 ccagacgtca aatgtctggt atccttggat gtcatgcaat attagacaaa ttgtagatga    3060
ttggcataaa gtagggaaaa aaatttatat gcctcctgca agtggattta acaatgagat    3120
aaggtgtact aatgatgtca cggaaatgtt ctttgaggtt cagaagaagg aagagaataa    3180
atatttaata aagtttatac ctcaagatga gatacaaaat cagtatacag cagtaggagc    3240
acattataaa ttggtgaaag tggatccat  agggttcgca cccacagatg tgcatagata    3300
ccatctacca gatgtaaagc agaagagagg agcagtcttg cttggaatgc tcggcctctt    3360
aggtttggca ggttccgcga tgggctcagt ggcgatagca ctgacggtcc agtcccaggc    3420
tttattgaat gggattgtgg agcagcagaa ggttctgctg agcctgatag atcagcactc    3480
cgagttatta aaactaacta tctgggtgt  aaaaaatctt caggcccgcc tcacagcctt    3540
ggaggaatac gtagcggacc aatcaagact ggcagtatgg ggatgctcat tctctcaagt    3600
atgccacact aatgtaaagt ggcctaatga ttcaatagtt cctaactgga cctcggaaac    3660
atggcttgaa tgggataaaa gagtgacagc aattacaaca aatatgacaa tagacttgca    3720
```

-continued

```
gagggcatat gaattggaac aaaagaatat gtttgagctt caaaaattag agatctcac   3780 ctcctgggcc agctggttcg acctcacgtg gtggtttaaa tatattaaga taggaattct   3840
tataataata gtgataatag acttagaat attagcttgc ttatggtcag tattaggcag    3900
gtttaggcag ggttaccgcc ctcttcctta tgtcttcaag ggagactatc accgacccca   3960
caacctcaaa cagccagaca agaaagagg agaagagcaa acagagaaa acagaacat     4020 cagctcagag aattacaggc caggatctgg cagagcttgg agcaaagagc aagtagagac   4080
ctggtggaag gagtccaggc tctacatttg gttgaagagc acacaagcag taattgaata   4140
tgggtggcaa gagctcaaag cagcaggagc agaaatatat aaaatattac agagcgctgc   4200
gcagaggcta tggagcggag gcaccaact cggactatca tgtattagag cagctacagc    4260 cttt ggcaga ggagtcagaa acattcctag acgcatcaga caaggagcag aagtcttact   4320
caactgagtt agacttaaga catcaacaag atgtaagcct ccccacagaa gaagaacagc   4380
cttgggaaga ggaagaggag gtaggctttc cagtctaccc acgacagcct gtgcatgaag   4440
ccacctataa agacttgata gacctgtccc actttttaaa agaaaagggg ggactggaag   4500
ggatttggtg gtctaaaaga agagaagaaa tcttggatat atatgcacaa aatgaatggg   4560
gaattatacc tgactggcag gcttacactt caggaccggg gatcaggtat ccaaaagcat   4620
ttgggttcct gtttaaactg atcccagtgg cagttccacc ggaacaagag aacaatgaat   4680
gcaataggct gctaaactct ctcagacag gaatccagga agatccatgg ggagaaaggc    4740
tcatgtggaa gtttgactct gctcttgcct atactttcta tgctcccata aagaggccag   4800
gagacttcaa gcatgtccaa agtcttagct atgaagctta taagaaggaa cctgactgct   4860
gcaagaggaa gtggtggcgc ttctagccga ccacagaggg ttgctatggc gataccctt    4920 aaaactgcta actctggagg gactttccac tagtgcatgc gcactggact ggggactttc   4980
caggatgacg ccgggtgggg gagtggtcag cccaatctgg ctgcatataa gcagctcgct   5040
ttgcgcttgt attgagtctc tccctgagag gctaccagat tgagcctagg ttgttctctg   5100
gtgagtcctt gaaggagtgc ctgcttgtag ccctgggcgg ttcgcaggcc cctggcttgt   5160
agctctgggt agctcgtcag gtgttctgga aggtcttgc taaggggacg cctttgcttg    5220
gtcttggtag acctctagca gtctcagtgg ccaggaggct gtgggattga ctaccgcttg   5280
cttgcctttg atgctcaata aagcttaccc gaattagaaa ggcattcaag tgtactcgct   5340
cattttgtct ttggtagaaa ctctggttac tggagatccc tcagatttgt gccagacttc   5400
tgatatctag tgagagtaga gaaaaatc                                     5428
```

<210> SEQ ID NO 22
<211> LENGTH: 9641
<212> TYPE: DNA
<213> ORGANISM: SIV - viral

<400> SEQUENCE: 22

```
trdctagaga tccctcagat ttgtgccaga cttctgatat ctagtgagag tagagaaaaa     60
tctccagcag tggcgcccga acagggactt gacgaagagc caagtcattc ccacctgtga   120
gggacagcgg cggcagccgg ccggaccgac ccacccggtg aagtgagtta accaaggagc   180
cccgacgcgc aggacacaag gtaagcggtg caccgtgctg tagtgagtgt gtgtccagga   240
tccgcttgag caggcgagat cgccgaggca accccagtag aaaaagaaaa gagggaagt    300 aaggccgagg caaagtgaaa gtaaaagaga tcctctgaga gaggaacag ggggcaataa    360 aattggcgcg agcgcgtcag gacttagggg aagagaattg gatgagctgg aaaagattag   420
```

-continued

```
gttacggccc tccggaaaga aaaatacca gctaaaacat gtgatatggg taagcaagga      480
actagataga tttggcctac atgaaaagtt gttagaaacc aaggaaggat gcgaaaaaat      540
tcttagcgta ctctttcctc tagttcctac agggtcagaa aatttaattt cgctgtacaa      600
cacctgctgt tgcatttggt gcgtacatgc gaaagtgaaa gtagcagata cagaagaggc      660
aaaagagaaa gtaaaacaat gctaccatct agtggttgaa aaacagaatg cagcctcaga      720 aaagaaaaa ggagcaacag tgacacctag tggccactca agaaattacc ccattcagat       780
agtaaatcaa accccagtac accagggaat ttctcccaga acactgaatg cttgggtaaa      840
atgtatagag gagaagaaat tcagcccaga aatagtgcct atgttcatag ctttgtcaga      900
aggatgcctc ccatacgacc tcaacggcat gctcaatgcc attggggacc atcagggagc      960
tctccaaata gtgaaagatg tcatcaatga cgaagctgca gactgggatc ttagacatcc     1020
tcagatgggg cctatgcccc aagggtgct aagaaaccca acaggagtg acatagcagg       1080 aaccaccagc agcatagaag aacaaattga atggacaact aggcagcaag atcaggtaaa     1140
tgtaggagga atttacaaac aatggatagt tctgggattg caaaaatgtg tgagcatgta     1200
caatccagtg aatattctag atataaaaca gggaccaaaa gaacccttta aggactatgt     1260
ggatcgattt tacaaagctc tgcgggcgga gcgaacagat ccacaagtga aaactggat      1320 gacgcagaca ttgctcatcc agaatgcaaa cccagattgt aaagccattc ttaagggatt     1380
aggcatgaac cccaccttgg aagaaatgtt attggcatgt caaggagtag ggggaccaaa     1440
gtataaagct caaatgatgg cagaagcaat gcaggaggtg caaggaaaaa ttatgatgca     1500 agcctcgggga ggaccaccgc ggggtccccc aaggcagcca cccagaaatc ctagatgccc     1560
caactgtgga aagtttggac atgtactgag agactgtaga gccccaagaa agcgaggatg     1620
cttcaagtgt ggagatccag acatctgat gagaaactgc caaagatgg tgaattttt       1680 agggaatgct ccctggggca gtggcaaacc caggaacttt cctgccgtgc cactgacccc     1740
aacggcaccc ccgatgccag gattagagga cccagcagag aagatgctac tggattacat     1800
gaagaagggg caacagatga aggcagagag ggaagccaaa cgggagaagg acaaaggccc     1860
ttacgaggcg gcttcaacct ccctcagttc tctctttgga acagaccaac tacagtagta     1920
gagatagagg ggcaaaaagt ggaggcccta ctagatacag gagcagatga cacagtaatc     1980
aaagatttac aattaacagg caattggaaa ccacaaatca taggaggaat tggaggagca     2040
attagggtaa agcaatattt caattgtaaa ataacagtgg caggtaaaag cactcatgct     2100
tcagtactag tgggccccac tcctgtaaat attataggta gaaatgtact taaaagtta      2160 ggatgtactt tgaactttcc tattagtaag atagaaacag taaggtaac actaaaacca      2220 ggaactgatg gaccaagaat caaacagtgg ccactgtcta agaaaagat tttagcctta     2280 caagaaatat gcaatcagat ggaaaagaa ggcaaaatct ctagaatagg tccagaaaat      2340
ccttacaaca caccagtgtt ttgtataaaa aagaaagatg gagccagctg gagaaaactg     2400
gtagatttta gacaattgaa taaagtgaca caggatttct ttgaggtgca gctaggaatc     2460
ccacatcctg gaggtctaaa acaatgtgaa cagatcacag tattggatat aggagatgcc     2520 tattttcat gcccattgga tgaggacttt agaaagtata ctgcattcac cattccatcg     2580
gtgaataatc agggcccagg aatcagatac cagtataatg tcctcccaca gggatggaaa     2640
ggctctccag caatttttca ggcaacagct gataaaatct tgaaaacatt caaagaagaa     2700
tacccagagg tattaattta tcagtatatg gatgatctgt tcgtgggaag tgacttaaat     2760
```

-continued

```
gccactgaac ataacaaaat gataaacaag ttgagagagc atctgagatt ctggggctc   2820 gagacccag ataagaagtt tcaaaaggaa cctccttttg aatggatggg atatgtgcta   2880
cacccaaaga aatggacagt gcagaaaata caactaccag aaaaagagca atggacagtg   2940
aatgatattc agaaattggt aggaaaactt aattgggcaa gtcagatata ttccggaatt   3000
aaaacaaaag agctctgtaa attgatcaga ggagcaaaac ctctagatga aatagtagaa   3060
tggacaagag aagcagaatt agagtatgaa gagaataaga taatagtgca ggaggaggtg   3120
catggagtgt actatcagcc agaaaaacca ctgatggcaa aagtacaaaa gttgacacaa   3180
ggacagtgga gttatcaaat agagcaagaa gaaaacaaac ctctcaaggc aggaaaatat   3240
gccaggacaa agaatgccca cacaaatgag ttaaggacac ttgcagggtt agtacaaaaa   3300
atagccaagg aatgcatagt aatctgggga agattgccaa aattttacct cccctggag   3360 agagaagtat gggatcaatg gtggcatgat tattggcagg taacatggat cccagagtgg   3420
gaattcatct caacaccacc attgataagg ctatggtaca acctcctgaa agaaccaatt   3480
ccaggagaag atgtatacta tgtagatggg gcagctaaca gaaattctaa agaaggcaag   3540
gcaggatact atacagcaag gggcaaaagt aaggtaatag ctttagaaaa tacaaccaat   3600
cagaaggcag agctgaaggc aatagaatta gccctaaaag attcaggacc aagagtaaac   3660
atagtaacag attcacagta tgcattaggc atactcacag catccccaga tcagtcagat   3720
aaccccatag ttagggaaat aattaaccctc atgatagcca aggaagcagt ctacctgtca   3780
tgggtaccag cccacaaggg tataggaggt aacgaacaaa tagacaaatt agtaagccaa   3840
ggaattaggc aagtactatt cctggaagga atagacagag ctcaggaaga acacgacaaa   3900
tatcataaca actggagagc tttagctcag gaattcagca tacctcctat agtggcaaaa   3960
gagatagttg cacaatgccc aaaatgccag ataaaggggg aacctattca tggccaggta   4020
gatgcaagtc ctgggacatg gcaaatggat tgcacccatc tagaaggaaa ggtcatcata   4080
gtggcagtcc atgtagccag tggatacctaa gaggcagaag taataccagc agagacagga   4140
aaagagacag cacatttcct gttaaagtta gcaggcaggt ggcctgtaaa acatttacac   4200
actgacaatg gccccaactt tgtcagtgaa aaggtagcca cagtctgttg gtgggctcaa   4260
atagagcaca ccacaggtgt accctataac ccccagagtc aggagtagt ggaagcaaag   4320 aatcatcatc ttaagacaat catagaacaa gttagggatc aagcagaaaa attagaaaca   4380
gcagtacaaa tggcagtatt aatacacaat tttaaaagaa aaggggggat aggggagtat   4440
agtccaggag aaagaatagt agatatcata accacagaca ttctaacaac taaattacaa   4500
caaatatttt caaaaattca aaattttcgg gtttattaca gagaaggaag ggatcaacag   4560
tggaaaggac cagcagaact catttggaaa ggagaaggcg ctgtggtgat taaagaaggg   4620
acagacttaa aggtggtacc aagaagaaaa gccaaaatca tcagagatta tggaaaagca   4680
gtggatagta attcccacat ggagagtaga gaggaatcag cttgagaaat ggaattcatt   4740
agtaaaatat cataaatata ggggagaaaa atacctagaa agatgggaac tataccacca   4800
tttccaatgc tcgggtgt ggacacactc tagaaaagat gtttactta aagatggctc   4860 agtaataagc attactgcct tctggaatct taccccagag aaaggatggt tgtctcaata   4920
tgcagttaca atagaatatg taaaagaaag ctattatact tacatagacc cagttacagc   4980
agacagaatg attcattggg aatatttccc atgttttaca gcccaggctg tgagaaaagt   5040
actgtttgga gaaagactaa tagcttgcta cagcccctgg ggacacaaag acaggtagg   5100 gactctacaa ttcctggctt tgcaagctta ccttcagtat tgtaaacatg gcagaaagag   5160
```

-continued

```
caccagaagt gccggaaggg gcaggagaga tacctctaga acagtggcta gaaagatcat    5220
tagaacaact caacagagag gcccggttac acttccaccc agagttcctt ttccgtcttt    5280
ggaacacttg tgtagaacat tggcatgata gacaccagag gagcctggag tatgcaaaat    5340
acagatatct tttgttggtg cataaggcca tgtttaccca tatgcaacag ggatgcccat    5400
gtagaaatgg gcacccaaga ggacctcctc ctccaggatt ggcctaattt ctgtcttgca    5460
gatggaacag ccacctgagg acgaggctcc acagagagaa ccttataatg aatggctgat    5520
agataccttg gcagaaatcc aggaagaagc tttgaagcat tttgataggc gcttgctaca    5580
tgcagtaggc tcatgggtgt atgagcaaca gggagacacc ttagaaggtg tccaaaagct    5640
aataactatt ctacaaagag ctttgttttt gcacttcagg catggatgca gggaaagccg    5700
cattggacaa gcaggaggga aatataattc cctcagatcc tttccaaggc cagacaaccc    5760
cttgtaataa atgctattgt aaaagatgtt gctatcactg ccagttatgc ttcttgcaga    5820
aagccttagg gatacattat catgtctaca gagtcaggag acctcgacag agattttttgg   5880 gcgaagtacc accacatagt gcagcaactg tggaaaggta agtaaaaagt aagtagacat    5940
gcttagatat atagttttag gaatagtcat aggattaggg ataggacacc aatgggttac    6000
agtgtattat ggaacaccta atggcaccc agctaggaca catctctttt gtgcaacaga    6060
taataattcc ttttgggtca caacaagttg tgtgcccagc ctattgcact atgaagaaca    6120
acacattccc aacataacag aaaacttcac aggcccccata acagagaatg aagtaataag    6180
acaagcatgg ggagctatct cttccatgat agatgcagtc ttaaaaccct gtgtaaagct    6240
gacaccatat tgtgtcaaga tgaaatgcac aaagggagat actgatacta cagaaaggac    6300
aacatccacc acttcctctt ggtccacatc cacccaacc tctacccccta tgactcccaa    6360 taccactgga ttagatatag actcaaacaa tacagaaccc acaacacaag agaatcggat    6420
atgtaaattt aatactacag gattatgtag agactgcaga ttggaaatag aagaaaactt    6480
cagatatcag gatataacat gtagaaatag tagtgaagat actgaagagt gctatatgac    6540
acattgtaac tcatcagtaa taacacagga ttgcaataag gcatcaacag ataaaatgac    6600
ttttaggttg tgtgcaccac caggatatgt cctgttgaga tgtagagaaa agctaaacca    6660
aaccaaattg tgtggcaata ttcagcagt gcaatgcact gacccaatgc ctgcaactat    6720
atccactatg tttggattta atgggaccaa acatgactat gatgagctaa ttttaacaaa    6780
ccctcaaaag ataaatgagt tcatgatca caagtatgta tatagagttg ataaaaaatg    6840
gaagctacag gtagtatgta gaagaaaagg gaatagatca ataatatcaa cgccaagtgc    6900
tacgggctta ttgttctatc atgggctaga accaggaaaa aatttaaaaa agggggatgtg   6960 ccagctgaag ggattatggg gaaaggccat gcaccaacta tcagaggaac ttagaaagat    7020
aaatggaagt atttatagaa aatggaatga gacagcaggc tgcagaaagc taaacaaaca    7080
gaacggtaca ggttgctcat tgaaaacaat agaagttagt gagtacacca cggagggcga    7140
tccgggggca gagacaatta tgcttctttg tggaggtgag tatttctttt gtaattggac    7200
aaagatttgg aagacatgga ataccagac gtcaaatgtc tggtatcctt ggatgtcatg    7260
caatattaga caaattgtag atgattggca taaagtaggg aaaaaaattt atatgcctcc    7320
tgcaagtgga tttaacaatg agataaggtg tactaatgat gtcacggaaa tgttctttga    7380
ggttcagaag aaggaagaga ataaatattt aataaagttt atacctcaag atgagataca    7440
aaatcagtat acagcagtag gagcacatta taaattggtg aaagtggatc ctatagggtt    7500
```

-continued

| | | | | |
|---|---|---|---|---|
| cgcacccaca | gatgtgcata | gataccatct | accagatgta | aagcagaaga gaggagcagt | 7560 |
| cttgcttgga | atgctcggcc | tcttaggttt | ggcaggttcc | gcgatgggct cagtggcgat | 7620 |
| agcactgacg | gtccagtccc | aggctttatt | gaatgggatt | gtggagcagc agaaggttct | 7680 |
| gctgagcctg | atagatcagc | actccgagtt | attaaaacta | actatctggg gtgtaaaaaa | 7740 |
| tcttcaggcc | cgcctcacag | ccttggagga | atacgtagcg | gaccaatcaa gactggcagt | 7800 |
| atggggatgc | tcattctctc | aagtatgcca | cactaatgta | aagtggccta atgattcaat | 7860 |
| agttcctaac | tggaccctcg | gaaacatggc | tgaatgggat | aaaagagtga cagcaattac | 7920 |
| aacaaatatg | acaatagact | tgcagagggc | atatgaattg | aacaaaaga atatgtttga | 7980 |
| gcttcaaaaa | ttaggagatc | tcacctcctg | ggccagctgg | ttcgacctca cgtggtggtt | 8040 |
| taaatatatt | aagataggaa | ttcttataat | aatagtgata | ataggactta gaatattagc | 8100 |
| ttgcttatgg | tcagtattag | gcaggtttag | gcagggttac | cgccctcttc cttatgtctt | 8160 |
| caagggagac | tatcaccgac | cccacaacct | caaacagcca | gacaaagaaa gaggagaaga | 8220 |
| gcaagacaga | gaaaaacaga | acatcagctc | agagaattac | aggccaggat ctggcagagc | 8280 |
| ttggagcaaa | gagcaagtag | agacctggtg | gaaggagtcc | aggctctaca tttggttgaa | 8340 |
| gagcacacaa | gcagtaattg | aatatggggtg | gcaagagctc | aaagcagcag gagcagaaat | 8400 |
| atataaaata | ttacagagcg | ctgcgcagag | gctatggagc | ggagggcacc aactcggact | 8460 |
| atcatgtatt | agagcagcta | cagcctttgg | cagaggagtc | agaaacattc ctagacgcat | 8520 |
| cagacaagga | gcagaagtct | tactcaactg | agttagactt | aagacatcaa caagatgtaa | 8580 |
| gcctccccac | agaagaagaa | cagccttggg | aagaggaaga | ggaggtaggc tttccagtct | 8640 |
| acccacgaca | gcctgtgcat | gaagccacct | ataaagactt | gatagacctg tcccactttt | 8700 |
| taaaagaaaa | ggggggactg | gaagggattt | ggtggtctaa | aagaagagaa gaatcttgg | 8760 |
| atatatatgc | acaaaatgaa | tggggaatta | tacctgactg | gcaggcttac acttcaggac | 8820 |
| cggggatcag | gtatccaaaa | gcatttgggt | tcctgtttaa | actgatccca gtggcagttc | 8880 |
| caccggaaca | agagaacaat | gaatgcaata | ggctgctaaa | ctcttctcag acaggaatcc | 8940 |
| aggaagatcc | atggggagaa | aggctcatgt | ggaagtttga | ctctgctctt gcctatactt | 9000 |
| tctatgctcc | cataaagagg | ccaggagact | tcaagcatgt | ccaaagtctt agctatgaag | 9060 |
| cttataagaa | ggaacctgac | tgctgcaaga | ggaagtggtg | gcgcttctag ccgaccacag | 9120 |
| agggttgcta | tggcgatacc | ctttaaaact | gctaactctg | gagggacttt ccactagtgc | 9180 |
| atgcgcactg | gactggggac | tttccaggat | gacgccgggt | ggggagtgg tcagcccaat | 9240 |
| ctggctgcat | ataagcagct | cgctttgcgc | ttgtattgag | tctctccctg agaggctacc | 9300 |
| agattgagcc | taggttgttc | tctggtgagt | ccttgaagga | gtgcctgctt gtagccctgg | 9360 |
| gcggttcgca | ggcccctggc | ttgtagctct | gggtagctcg | tcaggtgttc tggaaaggtc | 9420 |
| ttgctaaggg | gacgccttg | cttggtcttg | gtagacctct | agcagtctca gtggccagga | 9480 |
| ggctgtggga | ttgactaccg | cttgcttgcc | tttgatgctc | aataaagctt acccgaatta | 9540 |
| gaaaggcatt | caagtgtact | cgctcatttt | gtctttggta | gaaactctgg ttactggaga | 9600 |
| tccctcagat | ttgtgccaga | cttctgatat | ctagtgagag | t | 9641 |

<210> SEQ ID NO 23
<211> LENGTH: 518
<212> TYPE: PRT
<213> ORGANISM: SIV - viral

<400> SEQUENCE: 23

```
Ile Gly Ala Ser Ala Ser Gly Leu Arg Gly Arg Glu Leu Asp Glu Leu
 1               5                  10                  15
Glu Lys Ile Arg Leu Arg Pro Ser Gly Lys Lys Tyr Gln Leu Lys
            20                  25                  30
His Val Ile Trp Val Ser Lys Glu Leu Asp Arg Phe Gly Leu His Glu
            35                  40                  45
Lys Leu Leu Glu Thr Lys Glu Gly Cys Glu Lys Ile Leu Ser Val Leu
 50                  55                  60
Phe Pro Leu Val Pro Thr Gly Ser Glu Asn Leu Ile Ser Leu Tyr Asn
 65                  70                  75                  80
Thr Cys Cys Cys Ile Trp Cys Val His Ala Lys Val Lys Val Ala Asp
                    85                  90                  95
Thr Glu Glu Ala Lys Glu Lys Val Lys Gln Cys Tyr His Leu Val Val
                100                 105                 110
Glu Lys Gln Asn Ala Ala Ser Glu Lys Glu Lys Gly Ala Thr Val Thr
            115                 120                 125
Pro Ser Gly His Ser Arg Asn Tyr Pro Ile Gln Ile Val Asn Gln Thr
130                 135                 140
Pro Val His Gln Gly Ile Ser Pro Arg Thr Leu Asn Ala Trp Val Lys
145                 150                 155                 160
Cys Ile Glu Glu Lys Lys Phe Ser Pro Glu Ile Val Pro Met Phe Ile
                165                 170                 175
Ala Leu Ser Glu Gly Cys Leu Pro Tyr Asp Leu Asn Gly Met Leu Asn
                180                 185                 190
Ala Ile Gly Asp His Gln Gly Ala Leu Gln Ile Val Lys Asp Val Ile
                195                 200                 205
Asn Asp Glu Ala Ala Asp Trp Asp Leu Arg His Pro Gln Met Gly Pro
210                 215                 220
Met Pro Gln Gly Val Leu Arg Asn Pro Thr Gly Ser Asp Ile Ala Gly
225                 230                 235                 240
Thr Thr Ser Ser Ile Glu Glu Gln Ile Glu Trp Thr Thr Arg Gln Gln
                245                 250                 255
Asp Gln Val Asn Val Gly Gly Ile Tyr Lys Gln Trp Ile Val Leu Gly
                260                 265                 270
Leu Gln Lys Cys Val Ser Met Tyr Asn Pro Val Asn Ile Leu Asp Ile
            275                 280                 285
Lys Gln Gly Pro Lys Glu Pro Phe Lys Asp Tyr Val Asp Arg Phe Tyr
            290                 295                 300
Lys Ala Leu Arg Ala Glu Arg Thr Asp Pro Gln Val Lys Asn Trp Met
305                 310                 315                 320
Thr Gln Thr Leu Leu Ile Gln Asn Ala Asn Pro Asp Cys Lys Ala Ile
                325                 330                 335
Leu Lys Gly Leu Gly Met Asn Pro Thr Leu Glu Glu Met Leu Leu Ala
                340                 345                 350
Cys Gln Gly Val Gly Gly Pro Lys Tyr Lys Ala Gln Met Met Ala Glu
            355                 360                 365
Ala Met Gln Glu Val Gln Gly Lys Ile Met Met Gln Ala Ser Gly Gly
            370                 375                 380
Pro Pro Arg Gly Pro Arg Gln Pro Arg Asn Pro Arg Cys Pro
385                 390                 395                 400
Asn Cys Gly Lys Phe Gly His Val Leu Arg Asp Cys Arg Ala Pro Arg
                405                 410                 415
```

```
Lys Arg Gly Cys Phe Lys Cys Gly Asp Pro Gly His Leu Met Arg Asn
            420                 425                 430

Cys Pro Lys Met Val Asn Phe Leu Gly Asn Ala Pro Trp Gly Ser Gly
            435                 440                 445

Lys Pro Arg Asn Phe Pro Ala Val Pro Leu Thr Pro Thr Ala Pro Pro
            450                 455                 460

Met Pro Gly Leu Glu Asp Pro Ala Glu Lys Met Leu Leu Asp Tyr Met
465                 470                 475                 480

Lys Lys Gly Gln Gln Met Lys Ala Glu Arg Glu Ala Lys Arg Glu Lys
                    485                 490                 495

Asp Lys Gly Pro Tyr Glu Ala Ala Tyr Asn Ser Leu Ser Ser Leu Phe
            500                 505                 510

Gly Thr Asp Gln Leu Gln
            515

<210> SEQ ID NO 24
<211> LENGTH: 1016
<212> TYPE: PRT
<213> ORGANISM: SIV - viral

<400> SEQUENCE: 24

Phe Phe Arg Glu Cys Ser Leu Gly Gln Trp Gln Thr Gln Glu Leu Ser
1               5                   10                  15

Cys Arg Ala Thr Asp Pro Asn Gly Thr Pro Asp Ala Arg Ile Arg Gly
            20                  25                  30

Pro Ser Arg Glu Asp Ala Thr Gly Leu His Glu Glu Gly Ala Thr Asp
            35                  40                  45

Glu Gly Arg Glu Gly Ser Gln Thr Gly Glu Gly Gln Arg Pro Leu Arg
    50                  55                  60

Gly Gly Leu Gln Leu Pro Gln Phe Ser Leu Trp Asn Arg Pro Thr Thr
65                  70                  75                  80

Val Val Glu Ile Glu Gly Gln Lys Val Glu Ala Leu Leu Asp Thr Gly
                85                  90                  95

Ala Asp Asp Thr Val Ile Lys Asp Leu Gln Leu Thr Gly Asn Trp Lys
            100                 105                 110

Pro Gln Ile Ile Gly Gly Ile Gly Ala Ile Arg Val Lys Gln Tyr
            115                 120                 125

Phe Asn Cys Lys Ile Thr Val Ala Gly Lys Ser Thr His Ala Ser Val
130                 135                 140

Leu Val Gly Pro Thr Pro Val Asn Ile Ile Gly Arg Asn Val Leu Lys
145                 150                 155                 160

Lys Leu Gly Cys Thr Leu Asn Phe Pro Ile Ser Lys Ile Glu Thr Val
                165                 170                 175

Lys Val Thr Leu Lys Pro Gly Thr Asp Gly Pro Arg Ile Lys Gln Trp
            180                 185                 190

Pro Leu Ser Lys Glu Lys Ile Leu Ala Leu Gln Glu Ile Cys Asn Gln
            195                 200                 205

Met Glu Lys Glu Gly Lys Ile Ser Arg Ile Gly Pro Glu Asn Pro Tyr
    210                 215                 220

Asn Thr Pro Val Phe Cys Ile Lys Lys Asp Gly Ala Ser Trp Arg
225                 230                 235                 240

Lys Leu Val Asp Phe Arg Gln Leu Asn Lys Val Thr Gln Asp Phe Phe
                245                 250                 255

Glu Val Gln Leu Gly Ile Pro His Pro Gly Gly Leu Lys Gln Cys Glu
            260                 265                 270
```

```
Gln Ile Thr Val Leu Asp Ile Gly Asp Ala Tyr Phe Ser Cys Pro Leu
        275                 280                 285

Asp Glu Asp Phe Arg Lys Tyr Thr Ala Phe Thr Ile Pro Ser Val Asn
290                 295                 300

Asn Gln Gly Pro Gly Ile Arg Tyr Gln Tyr Asn Val Leu Pro Gln Gly
305                 310                 315                 320

Trp Lys Gly Ser Pro Ala Ile Phe Gln Ala Thr Ala Asp Lys Ile Leu
                325                 330                 335

Lys Thr Phe Lys Glu Glu Tyr Pro Glu Val Leu Ile Tyr Gln Tyr Met
                340                 345                 350

Asp Asp Leu Phe Val Gly Ser Asp Leu Asn Ala Thr Glu His Asn Lys
            355                 360                 365

Met Ile Asn Lys Leu Arg Glu His Leu Arg Phe Trp Gly Leu Glu Thr
        370                 375                 380

Pro Asp Lys Lys Phe Gln Lys Glu Pro Pro Phe Glu Trp Met Gly Tyr
385                 390                 395                 400

Val Leu His Pro Lys Lys Trp Thr Val Gln Lys Ile Gln Leu Pro Glu
                405                 410                 415

Lys Glu Gln Trp Thr Val Asn Asp Ile Gln Lys Leu Val Gly Lys Leu
                420                 425                 430

Asn Trp Ala Ser Gln Ile Tyr Ser Gly Ile Lys Thr Lys Glu Leu Cys
            435                 440                 445

Lys Leu Ile Arg Gly Ala Lys Pro Leu Asp Glu Ile Val Glu Trp Thr
        450                 455                 460

Arg Glu Ala Glu Leu Glu Tyr Glu Glu Asn Lys Ile Ile Val Gln Glu
465                 470                 475                 480

Glu Val His Gly Val Tyr Tyr Gln Pro Glu Lys Pro Leu Met Ala Lys
                485                 490                 495

Val Gln Lys Leu Thr Gln Gly Gln Trp Ser Tyr Gln Ile Glu Gln Glu
                500                 505                 510

Glu Asn Lys Pro Leu Lys Ala Gly Lys Tyr Ala Arg Thr Lys Asn Ala
            515                 520                 525

His Thr Asn Glu Leu Arg Thr Leu Ala Gly Leu Val Gln Lys Ile Ala
        530                 535                 540

Lys Glu Cys Ile Val Ile Trp Gly Arg Leu Pro Lys Phe Tyr Leu Pro
545                 550                 555                 560

Leu Glu Arg Glu Val Trp Asp Gln Trp Trp His Asp Tyr Trp Gln Val
                565                 570                 575

Thr Trp Ile Pro Glu Trp Glu Phe Ile Ser Thr Pro Pro Leu Ile Arg
                580                 585                 590

Leu Trp Tyr Asn Leu Leu Lys Glu Pro Ile Pro Gly Glu Asp Val Tyr
            595                 600                 605

Tyr Val Asp Gly Ala Ala Asn Arg Asn Ser Lys Glu Gly Lys Ala Gly
        610                 615                 620

Tyr Tyr Thr Ala Arg Gly Lys Ser Lys Val Ile Ala Leu Glu Asn Thr
625                 630                 635                 640

Thr Asn Gln Lys Ala Glu Leu Lys Ala Ile Glu Leu Ala Leu Lys Asp
                645                 650                 655

Ser Gly Pro Arg Val Asn Ile Val Thr Asp Ser Gln Tyr Ala Leu Gly
                660                 665                 670

Ile Leu Thr Ala Ser Pro Asp Gln Ser Asp Asn Pro Ile Val Arg Glu
            675                 680                 685
```

-continued

```
Ile Ile Asn Leu Met Ile Ala Lys Glu Ala Val Tyr Leu Ser Trp Val
    690                 695                 700
Pro Ala His Lys Gly Ile Gly Gly Asn Glu Gln Ile Asp Lys Leu Val
705                 710                 715                 720
Ser Gln Gly Ile Arg Gln Val Leu Phe Leu Glu Gly Ile Asp Arg Ala
                725                 730                 735
Gln Glu Glu His Asp Lys Tyr His Asn Asn Trp Arg Ala Leu Ala Gln
            740                 745                 750
Glu Phe Ser Ile Pro Pro Ile Val Ala Lys Glu Ile Val Ala Gln Cys
        755                 760                 765
Pro Lys Cys Gln Ile Lys Gly Glu Pro Ile His Gly Gln Val Asp Ala
    770                 775                 780
Ser Pro Gly Thr Trp Gln Met Asp Cys Thr His Leu Glu Gly Lys Val
785                 790                 795                 800
Ile Ile Val Ala Val His Val Ala Ser Gly Tyr Leu Glu Ala Glu Val
                805                 810                 815
Ile Pro Ala Glu Thr Gly Lys Glu Thr Ala His Phe Leu Leu Lys Leu
            820                 825                 830
Ala Gly Arg Trp Pro Val Lys His Leu His Thr Asp Asn Gly Pro Asn
        835                 840                 845
Phe Val Ser Glu Lys Val Ala Thr Val Cys Trp Trp Ala Gln Ile Glu
    850                 855                 860
His Thr Thr Gly Val Pro Tyr Asn Pro Gln Ser Gln Gly Val Val Glu
865                 870                 875                 880
Ala Lys Asn His His Leu Lys Thr Ile Ile Glu Gln Val Arg Asp Gln
                885                 890                 895
Ala Glu Lys Leu Glu Thr Ala Val Gln Met Ala Val Leu Ile His Asn
            900                 905                 910
Phe Lys Arg Lys Gly Gly Ile Gly Glu Tyr Ser Pro Gly Glu Arg Ile
        915                 920                 925
Val Asp Ile Ile Thr Thr Asp Ile Leu Thr Thr Lys Leu Gln Gln Asn
    930                 935                 940
Ile Ser Lys Ile Gln Asn Phe Arg Val Tyr Tyr Arg Glu Gly Arg Asp
945                 950                 955                 960
Gln Gln Trp Lys Gly Pro Ala Glu Leu Ile Trp Lys Gly Glu Gly Ala
                965                 970                 975
Val Val Ile Lys Glu Gly Thr Asp Leu Lys Val Val Pro Arg Arg Lys
            980                 985                 990
Ala Lys Ile Ile Arg Asp Tyr Gly Lys Ala Val Asp Ser Asn Ser His
        995                 1000                1005
Met Glu Ser Arg Glu Glu Ser Ala
    1010                1015

<210> SEQ ID NO 25
<211> LENGTH: 853
<212> TYPE: PRT
<213> ORGANISM: SIV - viral

<400> SEQUENCE: 25

Gln Trp Val Thr Val Tyr Tyr Gly Thr Pro Lys Trp His Pro Ala Arg
1               5                   10                  15
Thr His Leu Phe Cys Ala Thr Asp Asn Asn Ser Phe Trp Val Thr Thr
                20                  25                  30
Ser Cys Val Pro Ser Leu Leu His Tyr Glu Glu Gln His Ile Pro Asn
            35                  40                  45
```

-continued

```
Ile Thr Glu Asn Phe Thr Gly Pro Ile Thr Glu Asn Glu Val Ile Arg
 50                  55                  60
Gln Ala Trp Gly Ala Ile Ser Ser Met Ile Asp Ala Val Leu Lys Pro
 65                  70                  75                  80
Cys Val Lys Leu Thr Pro Tyr Cys Val Lys Met Lys Cys Thr Lys Gly
                 85                  90                  95
Asp Thr Asp Thr Thr Glu Arg Thr Thr Ser Thr Thr Ser Ser Trp Ser
                100                 105                 110
Thr Ser Thr Pro Thr Ser Thr Pro Met Thr Pro Asn Thr Thr Gly Leu
            115                 120                 125
Asp Ile Asp Ser Asn Asn Thr Glu Pro Thr Thr Gln Glu Asn Arg Ile
130                 135                 140
Cys Lys Phe Asn Thr Thr Gly Leu Cys Arg Asp Cys Arg Leu Glu Ile
145                 150                 155                 160
Glu Glu Asn Phe Arg Tyr Gln Asp Ile Thr Cys Arg Asn Ser Ser Glu
                165                 170                 175
Asp Thr Glu Glu Cys Tyr Met Thr His Cys Asn Ser Ser Val Ile Thr
            180                 185                 190
Gln Asp Cys Asn Lys Ala Ser Thr Asp Lys Met Thr Phe Arg Leu Cys
            195                 200                 205
Ala Pro Pro Gly Tyr Val Leu Leu Arg Cys Arg Glu Lys Leu Asn Gln
210                 215                 220
Thr Lys Leu Cys Gly Asn Ile Thr Ala Val Gln Cys Thr Asp Pro Met
225                 230                 235                 240
Pro Ala Thr Ile Ser Thr Met Phe Gly Phe Asn Gly Thr Lys His Asp
                245                 250                 255
Tyr Asp Glu Leu Ile Leu Thr Asn Pro Gln Lys Ile Asn Glu Phe His
            260                 265                 270
Asp His Lys Tyr Val Tyr Arg Val Asp Lys Lys Trp Lys Leu Gln Val
            275                 280                 285
Val Cys Arg Arg Lys Gly Asn Arg Ser Ile Ile Ser Thr Pro Ser Ala
290                 295                 300
Thr Gly Leu Leu Phe Tyr His Gly Leu Glu Pro Gly Lys Asn Leu Lys
305                 310                 315                 320
Lys Gly Met Cys Gln Leu Lys Gly Leu Trp Gly Lys Ala Met His Gln
                325                 330                 335
Leu Ser Glu Glu Leu Arg Lys Ile Asn Gly Ser Ile Tyr Arg Lys Trp
            340                 345                 350
Asn Glu Thr Ala Gly Cys Arg Lys Leu Asn Lys Gln Asn Gly Thr Gly
            355                 360                 365
Cys Ser Leu Lys Thr Ile Glu Val Ser Glu Tyr Thr Thr Glu Gly Asp
370                 375                 380
Pro Gly Ala Glu Thr Ile Met Leu Leu Cys Gly Gly Glu Tyr Phe Phe
385                 390                 395                 400
Cys Asn Trp Thr Lys Ile Trp Lys Thr Trp Asn Asn Gln Thr Ser Asn
                405                 410                 415
Val Trp Tyr Pro Trp Met Ser Cys Asn Ile Arg Gln Ile Val Asp Asp
            420                 425                 430
Trp His Lys Val Gly Lys Lys Ile Tyr Met Pro Pro Ala Ser Gly Phe
            435                 440                 445
Asn Asn Glu Ile Arg Cys Thr Asn Asp Val Thr Glu Met Phe Phe Glu
450                 455                 460
```

```
Val Gln Lys Lys Glu Glu Asn Lys Tyr Leu Ile Lys Phe Ile Pro Gln
465                 470                 475                 480

Asp Glu Ile Gln Asn Gln Tyr Thr Ala Val Gly Ala His Tyr Lys Leu
                485                 490                 495

Val Lys Val Asp Pro Ile Gly Phe Ala Pro Thr Asp Val His Arg Tyr
                500                 505                 510

His Leu Pro Asp Val Lys Gln Lys Arg Gly Ala Val Leu Leu Gly Met
            515                 520                 525

Leu Gly Leu Leu Gly Leu Ala Gly Ser Ala Met Gly Ser Val Ala Ile
530                 535                 540

Ala Leu Thr Val Gln Ser Gln Ala Leu Leu Asn Gly Ile Val Glu Gln
545                 550                 555                 560

Gln Lys Val Leu Leu Ser Leu Ile Asp Gln His Ser Glu Leu Leu Lys
                565                 570                 575

Leu Thr Ile Trp Gly Val Lys Asn Leu Gln Ala Arg Leu Thr Ala Leu
                580                 585                 590

Glu Glu Tyr Val Ala Asp Gln Ser Arg Leu Ala Val Trp Gly Cys Ser
            595                 600                 605

Phe Ser Gln Val Cys His Thr Asn Val Lys Trp Pro Asn Asp Ser Ile
610                 615                 620

Val Pro Asn Trp Thr Ser Glu Thr Trp Leu Glu Trp Asp Lys Arg Val
625                 630                 635                 640

Thr Ala Ile Thr Thr Asn Met Thr Ile Asp Leu Gln Arg Ala Tyr Glu
                645                 650                 655

Leu Glu Gln Lys Asn Met Phe Glu Leu Gln Lys Leu Gly Asp Leu Thr
                660                 665                 670

Ser Trp Ala Ser Trp Phe Asp Leu Thr Trp Trp Phe Lys Tyr Ile Lys
            675                 680                 685

Ile Gly Ile Leu Ile Ile Val Ile Ile Gly Leu Arg Ile Leu Ala
690                 695                 700

Cys Leu Trp Ser Val Leu Gly Arg Phe Arg Gln Gly Tyr Arg Pro Leu
705                 710                 715                 720

Pro Tyr Val Phe Lys Gly Asp Tyr His Arg Pro His Asn Leu Lys Gln
                725                 730                 735

Pro Asp Lys Glu Arg Gly Glu Gln Asp Arg Glu Lys Gln Asn Ile
                740                 745                 750

Ser Ser Glu Asn Tyr Arg Pro Gly Ser Gly Arg Ala Trp Ser Lys Glu
            755                 760                 765

Gln Val Glu Thr Trp Trp Lys Glu Ser Arg Leu Tyr Ile Trp Leu Lys
770                 775                 780

Ser Thr Gln Ala Val Ile Glu Tyr Gly Trp Gln Glu Leu Lys Ala Ala
785                 790                 795                 800

Gly Ala Glu Ile Tyr Lys Ile Leu Gln Ser Ala Ala Gln Arg Leu Trp
                805                 810                 815

Ser Gly His Gln Leu Gly Leu Ser Cys Ile Arg Ala Ala Thr Ala
            820                 825                 830

Phe Gly Arg Gly Val Arg Asn Ile Pro Arg Arg Ile Arg Gln Gly Ala
835                 840                 845

Glu Val Leu Leu Asn
    850

<210> SEQ ID NO 26
<211> LENGTH: 32
<212> TYPE: PRT
```

<213> ORGANISM: SIM27.ENV

<400> SEQUENCE: 26

Arg Leu Thr Ala Leu Glu Glu Tyr Val Ala Asp Gln Ser Arg Leu Ala
1               5                   10                  15

Val Trp Gly Cys Ser Phe Ser Gln Val Cys His Thr Asn Val Lys Trp
            20                  25                  30

<210> SEQ ID NO 27
<211> LENGTH: 32
<212> TYPE: PRT
<213> ORGANISM: SIV-Mandrill, MNDGB1

<400> SEQUENCE: 27

Arg Leu Thr Ser Leu Glu Asn Tyr Ile Lys Asp Gln Ala Leu Leu Ser
1               5                   10                  15

Gln Trp Gly Cys Ser Trp Ala Gln Val Cys His Thr Ser Val Glu Trp
            20                  25                  30

<210> SEQ ID NO 28
<211> LENGTH: 32
<212> TYPE: PRT
<213> ORGANISM: HIV1-N, YBF30

<400> SEQUENCE: 28

Lys Val Leu Ala Ile Glu Arg Tyr Leu Arg Asp Gln Gln Ile Leu Ser
1               5                   10                  15

Leu Trp Gly Cys Ser Gly Lys Thr Ile Cys Tyr Thr Thr Val Pro Trp
            20                  25                  30

<210> SEQ ID NO 29
<211> LENGTH: 32
<212> TYPE: PRT
<213> ORGANISM: HIV1-C, 96bw05.02

<400> SEQUENCE: 29

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Trp
            20                  25                  30

<210> SEQ ID NO 30
<211> LENGTH: 32
<212> TYPE: PRT
<213> ORGANISM: HIV1-O, ANT70C

<400> SEQUENCE: 30

Arg Leu Leu Ala Leu Glu Thr Leu Leu Gln Asn Gln Gln Leu Leu Ser
1               5                   10                  15

Leu Trp Gly Cys Lys Gly Lys Leu Val Cys Tyr Thr Ser Val Lys Trp
            20                  25                  30

<210> SEQ ID NO 31
<211> LENGTH: 32
<212> TYPE: PRT
<213> ORGANISM: SIV-CPZ, CPZGAB

<400> SEQUENCE: 31

Arg Leu Leu Ala Val Glu Arg Tyr Leu Gln Asp Gln Gln Ile Leu Gly
1               5                   10                  15

Leu Trp Gly Cys Ser Gly Lys Ala Val Cys Tyr Thr Thr Val Pro Trp
            20                  25                  30

<210> SEQ ID NO 32
<211> LENGTH: 32
<212> TYPE: PRT
<213> ORGANISM: HIV1-O, MVP5180

<400> SEQUENCE: 32

Arg Leu Gln Ala Leu Glu Thr Leu Ile Gln Asn Gln Gln Arg Leu Asn
1               5                   10                  15

Leu Trp Gly Cys Lys Gly Lys Leu Ile Cys Tyr Thr Ser Val Lys Trp
            20                  25                  30

<210> SEQ ID NO 33
<211> LENGTH: 32
<212> TYPE: PRT
<213> ORGANISM: SIV-1hoesti

<400> SEQUENCE: 33

Arg Leu Thr Ala Leu Glu Glu Tyr Val Lys His Gln Ala Leu Leu Ala
1               5                   10                  15

Ser Trp Gly Cys Gln Trp Lys Gln Val Cys His Thr Asn Val Glu Trp
            20                  25                  30

<210> SEQ ID NO 34
<211> LENGTH: 32
<212> TYPE: PRT
<213> ORGANISM: SIV-SYKES

<400> SEQUENCE: 34

Arg Leu Thr Ala Leu Glu Thr Tyr Leu Arg Asp Gln Ala Ile Leu Ser
1               5                   10                  15

Asn Trp Gly Cys Ala Phe Lys Gln Ile Cys His Thr Ala Val Thr Trp
            20                  25                  30

<210> SEQ ID NO 35
<211> LENGTH: 32
<212> TYPE: PRT
<213> ORGANISM: SIV-CPZ, CPZANT

<400> SEQUENCE: 35

Arg Met Leu Ala Val Glu Lys Tyr Leu Arg Asp Gln Gln Leu Leu Ser
1               5                   10                  15

Leu Trp Gly Cys Ala Asp Lys Val Thr Cys His Thr Thr Val Pro Trp
            20                  25                  30

<210> SEQ ID NO 36
<211> LENGTH: 32
<212> TYPE: PRT
<213> ORGANISM: SIV-CPZ-US

<400> SEQUENCE: 36

Arg Val Leu Ala Val Glu Arg Tyr Leu Lys Asp Gln Gln Ile Leu Gly
1               5                   10                  15

Leu Trp Gly Cys Ser Gly Lys Thr Ile Cys Tyr Thr Thr Val Pro Trp
            20                  25                  30

<210> SEQ ID NO 37
<211> LENGTH: 32
<212> TYPE: PRT
<213> ORGANISM: HIV1-F, 93br020.1

<400> SEQUENCE: 37

-continued

Arg Val Leu Ala Val Glu Arg Tyr Leu Lys Asp Gln Gln Leu Leu Gly
1               5                   10                  15

Leu Trp Gly Cys Ser Gly Lys Leu Ile Cys Thr Thr Asn Val Pro Trp
            20                  25                  30

<210> SEQ ID NO 38
<211> LENGTH: 32
<212> TYPE: PRT
<213> ORGANISM: HIV1-A, 92ug037

<400> SEQUENCE: 38

Arg Val Leu Ala Val Glu Arg Tyr Leu Arg Asp Gln Gln Leu Leu Gly
1               5                   10                  15

Ile Trp Gly Cys Ser Gly Lys Leu Ile Cys Pro Thr Asn Val Pro Trp
            20                  25                  30

<210> SEQ ID NO 39
<211> LENGTH: 32
<212> TYPE: PRT
<213> ORGANISM: HIV1-H, 90cr056

<400> SEQUENCE: 39

Arg Val Leu Ala Val Glu Arg Tyr Leu Arg Asp Gln Gln Leu Leu Gly
1               5                   10                  15

Ile Trp Gly Cys Ser Gly Lys Leu Ile Cys Thr Thr Asn Val Pro Trp
            20                  25                  30

<210> SEQ ID NO 40
<211> LENGTH: 32
<212> TYPE: PRT
<213> ORGANISM: HIV1-D, NDK

<400> SEQUENCE: 40

Arg Val Leu Ala Val Glu Arg Tyr Leu Arg Asp Gln Gln Leu Leu Gly
1               5                   10                  15

Ile Trp Gly Cys Ser Gly Arg His Ile Cys Thr Thr Asn Val Pro Trp
            20                  25                  30

<210> SEQ ID NO 41
<211> LENGTH: 32
<212> TYPE: PRT
<213> ORGANISM: HIV2-B, UC1

<400> SEQUENCE: 41

Arg Val Thr Ala Ile Glu Lys Tyr Leu Lys Asp Gln Ala Leu Leu Asn
1               5                   10                  15

Ser Trp Gly Cys Ala Phe Arg Gln Val Cys His Thr Thr Val Pro Trp
            20                  25                  30

<210> SEQ ID NO 42
<211> LENGTH: 32
<212> TYPE: PRT
<213> ORGANISM: SIV-D, MNE

<400> SEQUENCE: 42

Arg Val Thr Ala Ile Glu Lys Tyr Leu Lys Asp Gln Ala Gln Leu Asn
1               5                   10                  15

Ala Trp Gly Cys Ala Phe Arg Gln Val Cys His Thr Thr Val Pro Trp
            20                  25                  30

<210> SEQ ID NO 43
<211> LENGTH: 32

-continued

```
<212> TYPE: PRT
<213> ORGANISM: SIV-D, MM239

<400> SEQUENCE: 43
```

Arg Val Thr Ala Ile Glu Lys Tyr Leu Lys Asp Gln Ala Gln Leu Asn
1               5                   10                  15

Ala Trp Gly Cys Ala Phe Arg Gln Val Cys His Thr Thr Val Pro Trp
            20                  25                  30

```
<210> SEQ ID NO 44
<211> LENGTH: 32
<212> TYPE: PRT
<213> ORGANISM: SIV, SME543

<400> SEQUENCE: 44
```

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp
            20                  25                  30

```
<210> SEQ ID NO 45
<211> LENGTH: 32
<212> TYPE: PRT
<213> ORGANISM: SIV-D, SMM-PBJ-6P9

<400> SEQUENCE: 45
```

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp
            20                  25                  30

```
<210> SEQ ID NO 46
<211> LENGTH: 32
<212> TYPE: PRT
<213> ORGANISM: SIV-D, STM

<400> SEQUENCE: 46
```

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp
            20                  25                  30

```
<210> SEQ ID NO 47
<211> LENGTH: 32
<212> TYPE: PRT
<213> ORGANISM: HIV2-A, CAM2

<400> SEQUENCE: 47
```

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp
            20                  25                  30

```
<210> SEQ ID NO 48
<211> LENGTH: 32
<212> TYPE: PRT
<213> ORGANISM: HIV2-A, GH1

<400> SEQUENCE: 48
```

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp

<210> SEQ ID NO 49
<211> LENGTH: 32
<212> TYPE: PRT
<213> ORGANISM: HIV2-B, EHO

<400> SEQUENCE: 49

Arg Val Thr Ala Ile Glu Lys Tyr Leu Lys Asp Gln Ala Gln Leu Asn
1               5                   10                  15

Ser Trp Gly Cys Ala Phe Arg Gln Val Cys His Thr Thr Val Pro Trp
            20                  25                  30

<210> SEQ ID NO 50
<211> LENGTH: 32
<212> TYPE: PRT
<213> ORGANISM: SIV-SMM, PGM

<400> SEQUENCE: 50

Arg Val Thr Ala Ile Glu Lys Tyr Arg Lys Asp Gln Ala Gln Leu Asn
1               5                   10                  15

Ser Trp Gly Cys Ala Phe Arg Gln Val Cys His Thr Thr Val Pro Trp
            20                  25                  30

<210> SEQ ID NO 51
<211> LENGTH: 32
<212> TYPE: PRT
<213> ORGANISM: SIV-VERVET, AGM155

<400> SEQUENCE: 51

Arg Val Thr Ala Leu Glu Lys Tyr Leu Ala Asp Gln Ala Arg Leu Asn
1               5                   10                  15

Ala Trp Gly Cys Ala Trp Lys Gln Val Cys His Thr Thr Val Pro Trp
            20                  25                  30

<210> SEQ ID NO 52
<211> LENGTH: 32
<212> TYPE: PRT
<213> ORGANISM: SIV-VERVET, AGM3

<400> SEQUENCE: 52

Arg Val Thr Ala Leu Glu Lys Tyr Leu Glu Asp Gln Ala Arg Leu Asn
1               5                   10                  15

Ala Trp Gly Cys Ala Trp Lys Gln Val Cys His Thr Thr Val Pro Trp
            20                  25                  30

<210> SEQ ID NO 53
<211> LENGTH: 32
<212> TYPE: PRT
<213> ORGANISM: SIV-VERVET, AGMSAB1

<400> SEQUENCE: 53

Arg Val Thr Ala Leu Glu Lys Tyr Leu Glu Asp Gln Ala Arg Leu Asn
1               5                   10                  15

Ile Trp Gly Cys Ala Phe Arg Gln Val Cys His Thr Thr Val Leu Trp
            20                  25                  30

<210> SEQ ID NO 54
<211> LENGTH: 32
<212> TYPE: PRT
<213> ORGANISM: SIV-VERVET, AGMTY6

<400> SEQUENCE: 54

```
<210> SEQ ID NO 55
<211> LENGTH: 32
<212> TYPE: PRT
<213> ORGANISM: SIV-GRIVET, AGM677A

<400> SEQUENCE: 55

Arg Val Thr Ala Leu Glu Lys Tyr Leu Glu Asp Gln Ala Arg Leu Asn
1               5                   10                  15

Ser Trp Gly Cys Ala Trp Lys Gln Val Cys His Thr Thr Val Pro Trp
            20                  25                  30

<210> SEQ ID NO 56
<211> LENGTH: 32
<212> TYPE: PRT
<213> ORGANISM: SIV-VERVET, REV

<400> SEQUENCE: 56

Arg Val Thr Ala Leu Glu Lys Tyr Leu Glu Asp Gln Ala Arg Leu Asn
1               5                   10                  15

Val Trp Gly Cys Ala Trp Lys Gln Val Cys His Thr Thr Val Pro Trp
            20                  25                  30

<210> SEQ ID NO 57
<211> LENGTH: 32
<212> TYPE: PRT
<213> ORGANISM: SIV-TANTALUS, TAN1

<400> SEQUENCE: 57

Arg Val Thr Ala Leu Glu Lys Tyr Leu Glu Asp Gln Thr Arg Leu Asn
1               5                   10                  15

Leu Trp Gly Cys Ala Phe Lys Gln Val Cys His Thr Thr Val Pro Trp
            20                  25                  30
```